US008101661B2

(12) United States Patent
Mickle

(10) Patent No.: US 8,101,661 B2
(45) Date of Patent: *Jan. 24, 2012

(54) POLAR HYDROPHILIC PRODRUGS AND NON-STANDARD AMINO ACID CONJUGATES OF AMPHETAMINE AND OTHER STIMULANTS AND PROCESSES FOR MAKING AND USING THE SAME

(75) Inventor: Travis C. Mickle, Coralville, IA (US)

(73) Assignee: KemPharm, Inc., North Libery, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/843,169

(22) Filed: Jul. 26, 2010

(65) Prior Publication Data

US 2010/0292336 A1 Nov. 18, 2010

Related U.S. Application Data

(63) Continuation of application No. 11/953,668, filed on Dec. 10, 2007, now Pat. No. 7,776,917, application No. 12/843,169, which is a continuation of application No. 12/028,152, filed on Feb. 8, 2008, now Pat. No. 7,772,222.

(60) Provisional application No. 60/888,870, filed on Feb. 8, 2007, provisional application No. 60/869,375, filed on Dec. 11, 2006.

(51) Int. Cl.
*A61K 31/196* (2006.01)
*A61K 31/16* (2006.01)
*A61P 25/00* (2006.01)

(52) U.S. Cl. ........................ 514/561; 514/613

(58) Field of Classification Search .................. 514/561, 514/613
See application file for complete search history.

(56) References Cited

U.S. PATENT DOCUMENTS

| | | | |
|---|---|---|---|
| 2,881,113 A | 4/1959 | Millman | |
| 2,892,753 A | 6/1959 | Schmidt | |
| 6,417,184 B1 | 7/2002 | Ockert | |
| 6,475,494 B2 | 11/2002 | Kaiko et al. | |
| 6,503,950 B1 | 1/2003 | Ockert | |
| 6,525,062 B2 | 2/2003 | Levine | |
| 6,696,066 B2 | 2/2004 | Kaiko et al. | |
| 7,105,486 B2 | 9/2006 | Mickle et al. | |
| 7,223,735 B2 | 5/2007 | Mickle et al. | |
| 7,772,222 B2 | 8/2010 | Mickle | |
| 7,776,917 B2 | 8/2010 | Mickle | |
| 2005/0038121 A1 | 2/2005 | Mickle et al. | |
| 2005/0054561 A1 | 3/2005 | Mickle et al. | |
| 2006/0177892 A1 | 8/2006 | De Frees | |

FOREIGN PATENT DOCUMENTS

| | | |
|---|---|---|
| CN | 1816346 A | 8/2006 |
| FR | 1421130 | 3/1966 |
| WO | 03/072046 | 9/2003 |
| WO | 2007/033099 | 3/2007 |
| WO | 2008/073918 | 6/2008 |
| WO | 2008/098151 | 8/2008 |

OTHER PUBLICATIONS

European Patent Office, Communication dated Jun. 8, 2010, in EP Application No. 07 869 098.9.
Amy Sorter, Understanding ADHD Stimulant Abuse, Publication, Vitality Drug Free Work, 2002. (http://12.42.224.168/HealthyLiving/familyhome/jan04familyhomestimulantabuse.htm).
International Preliminary Report on Patentability for PCT International Application No. PCT/US08/53363, dated Nov. 6, 2008.
Davankova et al., "Synthesis and Pharmacological Properties of N Aminoacyl Derivatives of Beta Phenyl ISO Propylamine." Pharmaceutical Chemistry Journal, vol. 9, No. 3, 1975.
G.C. Barrett, D.T. Elmore; Methods for Peptide Bonds Amino Acids and Peptides; 1st Edition, Cambridge University Press, UK, 1998, pp. 151-156.
International Search Report and Written Opinion corresponding to International Application Serial No. PCT/US08/53363, mailed Nov. 6, 2008, 19 pages.
J. Jones; Amino Acid and Peptide Synthesis; 2nd Edition, Oxford University Press, UK, 2002, pp. 25-41.
Musshoff, "Illegal or legitimate use? Precursor compounds to amphetamine and methamphetamine." Drug Metabolism Reviews 2000 US, vol. 32, No. 1, pp. 15-44.
Office Action in U.S. Appl. No. 11/953,668, dated Dec. 16, 2009.
Office Action in U.S. Appl. No. 11/953,668, dated Jun. 5, 2009.
Office Action in U.S. Appl. No. 11/953,668, dated Mar. 19, 2009.
Office Action in U.S. Appl. No. 12/028,152, dated Feb. 16, 2010.
Office Action in U.S. Appl. No. 12/028,152, dated Feb. 23, 2010.
Office Action in U.S. Appl. No. 12/028,152, dated Mar. 20, 2009.
Office Action in U.S. Appl. No. 12/028,152, dated Nov. 12, 2008.
Office Action in U.S. Appl. No. 12/028,152, dated Nov. 13, 2009.
The Drug Enforcement Administration Office of Diversion Control and Office of Congressional and Public Affairs Demand Reduction Section, Stimulant Abuse by School Age Children: A Guide for School Officials; Publication, Developed and Published by The Drug Enforcement Administration Office of Diversion Control and Office of Congressional and Public Affairs Demand Reduction Section; Jun. 2001. (http://www.deadiversion.usdoj.gov/pubs/brochures/stimulant/stimulant_abuse.htm).
European Search Report for European Patent Application No. 07869098.9-2112, dated Dec. 10, 2009.
Notice of Allowance in U.S. Appl. No. 11/953,668, dated Apr. 7, 2010.
Notice of Allowance in U.S. Appl. No. 12/028,152, dated Apr. 12, 2010.
Berge et al., Pharmaceutical Salts, J. Pharm. Sci., 66(1):1-19 (1977).
Office Action in U.S. Appl. No. 12/473,903, dated Apr. 13, 2011.
Office Action in U.S. Appl. No. 12/473,903, dated Aug. 4, 2010.
Office Action in U.S. Appl. No. 12/473,903, dated Sep. 15, 2010.
Office Action in U.S. Appl. No. 12/477,616, dated Jun. 28, 2011.
Structure-Activity Relationship and Drug Design, Remington's Pharmaceutical Sciences (Sixteenth Edition). Mack Publishing, 1980. pp. 420-425.

*Primary Examiner* — Sreeni Padmanabhan
*Assistant Examiner* — Sahar Javanmard
(74) *Attorney, Agent, or Firm* — McAndrews, Held & Malloy, Ltd.

(57) ABSTRACT

Disclosed are polar, hydrophilic stimulant prodrug compositions comprising at least one stimulant chemically attached to a polar hydrophilic ligand, a salt thereof, a derivative thereof, or a combination thereof. Also disclosed are non-standard amino acid conjugates of amphetamine. Methods of making and using the same are also disclosed.

16 Claims, 5 Drawing Sheets

POLAR HYDROPHILIC PRODRUGS AND NON-STANDARD AMINO ACID CONJUGATES OF AMPHETAMINE AND OTHER STIMULANTS AND PROCESSES FOR MAKING AND USING THE SAME

RELATED APPLICATIONS

This application is a continuation of U.S. patent application Ser. No. 11/953,668, filed on Dec. 10, 2007 now U.S. Pat. No. 7,776,917, which claims priority to and benefit of U.S. provisional patent application No. 60/869,375, filed on Dec. 11, 2006; and a continuation of U.S. patent application Ser. No. 12/028,152, filed on Feb. 8, 2008 now U.S. Pat. No. 7,772,222, which claims priority to and benefit of U.S. provisional patent application No. 60/888,870, filed on Feb. 8, 2007.

BACKGROUND OF THE INVENTION

The present technology describes, in general, novel prodrugs/compositions of the stimulant amphetamine (i.e., 1-phenylpropan-2-amine). The present technology also describes polar hydrophilic conjugates of amphetamine, salts thereof, other derivatives thereof, and combinations thereof, as well as non-standard amino acid conjugates of amphetamine, salts thereof, other derivatives thereof, and combinations thereof. Additionally, the presently described technology also relates generally to the methods of making and using these new prodrugs/compositions.

The presently described technology in at least one aspect is focused on a slow/sustained controlled release composition of amphetamine, in prodrug form, that allows slow/sustained/controlled delivery of the stimulant into the blood system of a human or animal within a safe therapeutic window upon oral administration. At least some compositions/formulation of the current technology can lessen the rebound effect, cardiovascular stress, addiction/abuse potential and/or other common stimulant side effects associated with amphetamine and similar compounds. Such compositions may also increase the duration of therapeutic efficacy, ease of application, patient compliance and/or any combination of these characteristics when administered, in particular, orally.

Stimulants, including amphetamine and its derivatives, enhance the activity of the sympathetic nervous system and/or central nervous system (CNS) and are prescribed for the treatment of a range of conditions and disorders predominantly encompassing, for example, attention deficit hyperactivity disorder (ADHD), attention deficit disorder (ADD), obesity, narcolepsy, appetite suppression, depression, anxiety and wakefulness.

Attention deficit hyperactivity disorder (ADHD) in children has been treated with stimulants for many years. However, more recently, the increase in the number of prescriptions for ADHD therapy in an adult population has, at times, outperformed the growth of the pediatric market. Although there are various drugs currently in use for the treatment of ADHD, such as methylphenidate (commercially available from, for example, Novartis International AG (located in Basel, Switzerland) under the trademark Ritalin®) and non-stimulant atomoxetine (commercially from Eli Lilly and Company (located in Indianapolis, Ind.) as Strattera®), amphetamine has been the forerunner in ADHD therapy. Moreover during classroom trials, non-stimulants have shown to be less effective in improving behavior and attention of ADHD afflicted children than amphetamine derivatives.

Initial drug therapy for ADHD was limited to fast acting immediate release formulations of stimulants (e.g., Dexedrine®, pure dextroamphetamine sulfate, commercially available from Smith Kline and French located in the United Kingdom) which triggered an array of potentially undesirable side effects including, for example, fast wear-off of the therapeutic effect of the stimulant active ingredient causing rebound symptoms, cardiovascular stress/disorders (e.g., increased heart rate, hypertension, cardiomyopathy), other side effects (e.g., insomnia, euphoria, psychotic episodes), addiction and abuse.

Behavioral deterioration (rebound/"crashing") is observed in a significant portion of children with ADHD as the medication wears off, typically in the afternoon or early evening. Rebound symptoms include, for example, irritability, crankiness, hyperactivity worse than in the unmedicated state, sadness, crying and in rare cases psychotic episodes. The symptoms may subside quickly or last several hours. Some patients may experience rebound/crashing so severe that treatment must be discontinued. Rebound/crashing effects can also give rise to addictive behavior by enticing patients to administer additional doses of stimulant with the intent to prevent anticipated rebound/crashing negative outcomes and side effects.

Stimulants, such as methylphenidate and amphetamine, have shown to exhibit noradrenergic and dopaminergic effects that can lead to cardiovascular events comprising, for example, increased heart rate, hypertension, palpitations, tachycardia and in isolated cases cardiomyopathy, stroke, myocardial infarction and sudden death. Consequently, currently available stimulants expose patients with pre-existing structural cardiac abnormalities or other severe cardiac indications to even greater health risks and are frequently not used or used with caution in this population. It is notable, however that the cardiovascular effects of stimulants, for example on heart rate and blood pressure, is dependent on the administered dose. As a result, a treatment which maintains the lowest effective stimulant blood concentrations for a therapeutically beneficial duration is believed to demonstrate fewer cardiovascular risks/side effects.

Amphetamine and many of its derivatives (e.g., methamphetamine, 3,4-methylenedioxy-methamphetamine/"Ecstasy") are widely abused for various purposes such as euphoria, extended periods of alertness/wakefulness, or rapid weight loss or by actual ADHD patients who developed excessive self-dosing habits to prevent rebound symptoms from manifesting, for example, in anxiety or depression. The effects desired by potential abusers originated from the stimulation of the central nervous system and prompted a Schedule II or even Schedule I classification for amphetamine (d- and l-amphetamine individually and any combination of both are Schedule II) and certain derivatives thereof after passage of the Controlled Substance Act (CSA) in 1970. Both classifications are defined by the high propensity for abuse. Schedule II drugs have an accepted medical use while Schedule I substances do not pursuant to the CSA. So far, all amphetamine products, including compositions with sustained release formulations and prodrugs thereof, are obligated to include a black box warning on the drug label to inform patients about the potential for amphetamine abuse and dependence.

It has been observed in the conventional art that most side effects of amphetamines are caused by a large initial spike in blood concentration of the stimulant which quickly erodes to levels below therapeutic effectiveness (typically within 4-6 hours). As a consequence, the high potency of dextroamphetamine (d-amphetamine) was subsequently modulated by a series of new drugs with increasingly sustained release profiles achieved by delivering amphetamine more slowly into the blood stream with the goal to create safer and less abusable treatment outcomes and regimens. The methods and technologies for generating smaller spikes in drug blood concentrations include, for example, use of mixed salts and isomer compositions (i.e., different salts of d- and less potent l-amphetamine), extended/controlled/sustained release formulations (e.g., Adderall XR® commercially available from Shire U.S., Inc. located in Wayne, Pa.) and, most recently, prodrugs of amphetamine (Vyvanse™ also commercially available from Shire). The ideal drug treatment option should produce stimulant blood concentrations within a narrow therapeutic window for an extended time duration followed by a prolonged fade-out period in order to minimize cardiovascular stress and behavioral deterioration, and would also exhibit anti-abuse properties.

Besides immediate release formulations, newer sustained release formulations have been developed with the objective to provide a therapeutic treatment option that offers the convenience of a single daily dosing regimen versus multiple quotidian administrations. Such formulations also have the objective of imparting or rendering a euphoric response. Sustained release formulations commonly consist of drug particles coated with a polymer or polymer blend that delays and extends the absorption of the active drug substance by the gastrointestinal tract for a relatively defined period of time. Such formulations frequently embed the therapeutic agent/active ingredient/drug within a hydrophilic hydrocolloid gelling polymer matrix (e.g., hydroxypropyl methylcellulose, hydroxypropyl cellulose or pullulan). This dosage formulation in turn becomes a gel upon entering an acidic medium, as found in the stomach of humans and animals, thereupon slowly effusing the therapeutic agent/active ingredient/drug. However, the dosage formulation dissolves in an alkaline medium, as found in the intestines of humans and animals, concurrently liberating the drug more quickly in an uncontrolled manner. Some formulations, such as acrylic resins, acrylic latex dispersions, cellulose acetate phthalate, and hydroxypropyl methylcellulose phthalate, offer improved sustained release in the intestines by being resistant to acidic environments and dispensing the active ingredient only at elevated pH via a diffusion-erosion mechanism, either by themselves or mixed with hydrophilic polymers.

Sustained release formulations have been moderately effective in providing an improved and extended dosage form over immediate release tablets. Nonetheless, such formulations are potentially subject to inconsistent, erratic or premature release of the therapeutic agent due to failure of the polymer material, and they also usually allow easy extraction of the active ingredient utilizing a simple physical procedure. Since single daily dose formulations contain a greater amount of amphetamine than immediate release formulations, they are more attractive to potential abusers, consequently making the extractability of drug substance an additional undesirable property. It is also, at least in part, a reason for increased drug diversion, especially evident by selling or trading of medication by school children who are ADHD patients and in possession of sustained release amphetamine capsules. The obtained stimulants are then abused by classmates without the disorder by either ingesting high doses or snorting the drug material after crushing it.

U.S. Pat. No. 7,105,486 (to assignee New River Pharmaceuticals, hereinafter the "'486 patent") appears to describe compounds comprising a chemical moiety (namely l-lysine) covalently attached to amphetamine, compositions thereof, and methods of using the same. Allegedly, these compounds and their compositions are useful for reducing or preventing abuse and overdose of amphetamine. The '486 patent also describes that using any amino acid other than l-lysine (Table 46) will not give rise to the same in vivo properties demonstrated by l-lysine-d-amphetamine (Lys-Amp, Vyvanse™). Additionally, since lysine is a natural and standard amino acid, the breakdown of the new prodrug occurs faster than desired to reduce the side effect profile. Thus, quick release of amphetamine from such standard amino acid conjugate compositions may cause an increase in blood pressure and heart rate found in other conventional stimulant treatments. As a result, there still exists a need within the art for a safer dosage form of amphetamine, and treatment regimen that is therapeutically effective and can provide sustained release and sustained therapeutic effect.

BRIEF SUMMARY OF THE INVENTION

The presently described technology provides, in part, compositions comprising at least one amphetamine conjugated with a non-standard amino acid, or a salt thereof, which can diminish or eliminate pharmacological activity of the amphetamine until released in vivo. The non-standard amino acid conjugate(s) of the present technology is amphetamine in a prodrug form, and can be converted into its active form in the body by normal metabolic processes. Although not wanting to be bound by any particular theory, one or more non-standard amino acid conjugates of the present technology are believed to be safer than other sustained release forms of amphetamine by providing controlled blood levels for a prolonged period of time, thus preventing the rebound effect, cardiovascular stress and euphoria associated with conventional stimulant treatment options.

The presently described technology further provides methods of controlled therapeutic delivery of amphetamine compositions by oral administration. Release of amphetamine following oral administration of the non-standard amino acid conjugates of the present technology can occur gradually over an extended period of time thereby eliminating unintended elevations (e.g., blood level concentration spikes) of drug levels in the bloodstream of a human or animal patient. Again not wanting to be bound by any particular theory, it is also believed that such spikes in blood levels can lead to a euphoric drug "high" and cardiovascular effects like increased blood pressure and heart rate. Additionally, sustained blood levels are achieved within an effective therapeutic range for a longer duration than other conventional therapies, thereby preventing a rebound effect.

At least some compositions comprising the amphetamine prodrugs of the present technology are resistant to abuse by parenteral routes of administration, such as intravenous "shooting," intranasal "snorting," or inhalation "smoking," that are often employed during illicit use. The present technology thus provides a stimulant based treatment modality and dosage form for certain disorders requiring the stimulation of the CNS such as ADHD, ADD, obesity, narcolepsy, appetite suppressant, depression, anxiety, and wakefulness with reduced or prevented abuse potential. Although not wanting to be bound by any particular theory, it is believed that the treatment of such CNS conditions as noted above with compositions of the present technology results in substantially decreased abuse liability as compared to existing stimulant treatment modalities and dosage forms.

At least some compositions comprising the amphetamine prodrugs of the present technology can also be used for treating stimulant (cocaine, methamphetamine) abuse and addiction, for improving battle field alertness, and/or for combating fatigue.

In a first aspect, the presently described technology provides a composition comprising at least one non-standard amino acid conjugate of amphetamine, a salt thereof, a derivative thereof, or a combination thereof. Preferably, the non-standard amino acid is covalently attached to amphetamine through the C-terminus of the non-standard amino acid. The N-terminus or the side chain amino group of the non-standard amino acid may be in a free and unprotected state, or in the form of a salt thereof. The non-standard amino acid moiety can be derived from a non-standard amino acid that is either a dextro- (d-) or levo- (l-) form amino acid, racemic amino acid, or a mixture thereof.

In accordance with some embodiments, non-standard amino acids are used. Examples of preferred non-standard amino acids to be conjugated with the amphetamine include, but are not limited to, homoarginine, selenomethionine, citrulline, and homocitrulline. Homoarginine is most preferred for at least some embodiments of the present technology.

The compositions of the present technology preferably have no or a substantially decreased pharmacological activity when administered through injection or intranasal routes of administration. However, they remain orally bioavailable. The bioavailability can be a result of the hydrolysis of the covalent linkage following oral administration. Hydrolysis is time-dependent, thereby allowing amphetamine and other metabolites such as p-hydroxyamphetamine and p-hydroxyephedrine to become available in its active form over an extended period of time. In at least one further embodiment, release of amphetamine is diminished or eliminated when the composition of the present technology is delivered by parenteral routes.

For example, in one embodiment, the composition of the present technology maintains its effectiveness and abuse resistance following the crushing of the tablet, capsule or other oral dosage form utilized to deliver the therapeutic component (i.e., active ingredient/drug) due to the inherent controlled release components being a property of the composition not formulation. In contrast, conventional extended release formulations used to control the release of amphetamine are subject to release of up to the entire amphetamine content immediately following crushing. When the content of the crushed tablet is injected or snorted, the large dose of amphetamine produces the "rush" effect sought by addicts.

In another aspect, the presently described technology provides a method for treating a human or animal patient with a disorder or condition requiring the stimulation of the patient's CNS (Central Nervous System), comprising the step of orally administering to the patient in need a composition formulated for oral dosage comprising at least one non-standard amino acid conjugate of amphetamine of the present technology, wherein the blood levels of amphetamine in the patient's body can maintain a therapeutically effect level throughout a given day, and do not lead to behavioral deterioration or the rebound effect.

In another aspect, the presently described technology provides a method for treating a human or animal patient with a disorder or condition requiring the stimulation of the patient's CNS (Central Nervous System), comprising the step of orally administering to the patient in need a composition formulated for oral dosage comprising at least one non-standard amino acid conjugate of amphetamine of the present technology, wherein the blood levels of amphetamine in the patient's body are not unnecessarily elevated (i.e., blood level spikes) thus preventing additional cardiovascular stress through, for example, increased blood pressure and/or heart rate.

In another aspect, the presently described technology provides a method for treating a human or animal patient with a disorder or condition requiring the stimulation of the patient's CNS, comprising orally administering to the patient in need a composition formulated for oral dosage comprising at least one non-standard amino acid conjugate of amphetamine, wherein the blood levels of amphetamine in the patient's body can maintain a therapeutically effect level, but do not result in an euphoric effect (such as that observed with abuse of amphetamines).

In a further aspect, the presently described technology provides a method for delivering amphetamine, comprising providing a human or animal patient with a therapeutically effective amount of at least one non-standard amino acid conjugate of amphetamine, which can provide a therapeutically bioequivalent area under the curve (AUC) when compared to free amphetamine, but does not provide a maximum plasma concentration ($C_{max}$) which results in an increased heart rate, increased blood pressure or drug related euphoria when taken orally.

In another aspect, the presently described technology provides a composition for treating a human or animal patient having attention deficit disorder or attention deficit hyperactivity disorder, comprising amphetamine chemically attached to a polar hydrophilic ligand, a salt thereof, or a combination thereof.

In an additional aspect, the presently described technology provides a composition for treating a human or animal patient having attention deficit disorder or attention deficit hyperactivity disorder, comprising amphetamine chemically attached to a polar hydrophilic ligand, a salt thereof, or a combination thereof, wherein the polar hydrophilic ligand is homoarginine.

In a further aspect, the presently described technology provides a composition for treating a human or animal patient having attention deficit disorder or attention deficit hyperactivity disorder, comprising amphetamine chemically attached to a polar hydrophilic ligand, a salt thereof, or a combination thereof, wherein the polar hydrophilic ligand is l-homoarginine.

In another aspect, the presently described technology provides a composition for treating a human or animal patient having attention deficit disorder or attention deficit hyperactivity disorder, comprising amphetamine chemically attached to a polar hydrophilic ligand, a salt thereof, or a combination thereof, wherein the amphetamine is d-amphetamine.

In an additional aspect, the presently described technology provides a composition for treating a human or animal patient having attention deficit disorder or attention deficit hyperactivity disorder, comprising amphetamine chemically attached to a polar hydrophilic ligand, a salt thereof, or a combination thereof, wherein the salt thereof is an acefyllinate, 4-acetamidobenzoate, acetate, aceturate, adipate, aminosalicylate, ammonium, ascorbate, l-aspartate, benzoate, besylate, bicarbonate, borate, butyrate, calcium, camphocarbonate, camphorate, d-camsylate, l-camsylate, camsylate, carbonate, cholate, citrate, cypionate, decanoate, dichloroacetate, edentate, edisylate, estolate, esylate, ethyl sulfate, fumarate, furate, fusidate, galactarate (mucate), galacturonate, gallate, gentisate, gluceptate, gluconate, glucuronate, glutamate, glutarate, glycerophosphate, glycolate, heptanoate (enanthate), hexanoate, hippurate, hybenzate, hydrobromide/bromide, hydrochloride/chloride, hydroxide, hydroxybenzoate, iodide, isethionate, d-lactate, l-lactate, d,l-lactate, lactobionate, laurate, lithium, magnesium, malate, d,l-malate, maleate, malonate, mandelate, meso-tartrate, mesylate, methanesulfonate, methylsulfate, myristate, napadisilate, 2-napsylate, nicotinate, nitrate, octanoate, oleate, orotate, oxalate, palmitate, pamoate, phenylpropionate, phosphate, picrate, pivalate, potassium, propionate, pyrophosphate, salicylate, salicylsulfate, sodium, stearate, succinate, sulfate, sulfosalicylate, tannate, d-tartrate, l-tartrate, d,l-tartrate, terephthalate, thiocyanate, thiosalicylate, tosylate, tribrophenate, triflate, undecylenate, valerate, valproate, xinafoate, zinc, and mixtures thereof.

In a further aspect, the presently described technology provides a composition for treating a human or animal patient having attention deficit disorder or attention deficit hyperactivity disorder, comprising amphetamine chemically attached to a polar hydrophilic ligand, a salt thereof, or a combination thereof, wherein the salt thereof is a mesylate, a hydrochloride salt, a sulfate, an oxalate, a triflate, a citrate, a malate, a tartrate, a phosphate, a nitrate, a benzoate, or a mixture thereof.

Another aspect of the present technology provides a composition for treating a human or animal patient having attention deficit disorder or attention deficit hyperactivity disorder, comprising a derivative of amphetamine chemically attached to a polar hydrophilic ligand, a salt thereof, or a combination thereof.

In an additional aspect, the present technology provides a composition for treating a human or animal patient having attention deficit disorder or attention deficit hyperactivity disorder, comprising a derivative of amphetamine chemically attached to a polar hydrophilic ligand, a salt thereof, or a combination thereof wherein the polar hydrophilic ligand is homoarginine.

In a further aspect, the present technology provides a composition for treating a human or animal patient having attention deficit disorder or attention deficit hyperactivity disorder, comprising a derivative of amphetamine chemically attached to a polar hydrophilic ligand, a salt thereof, or a combination thereof wherein the polar hydrophilic ligand is l-homoarginine.

In another aspect, the present technology provides a composition for treating a human or animal patient having attention deficit disorder or attention deficit hyperactivity disorder, comprising a derivative of amphetamine chemically attached to a polar hydrophilic ligand, a salt thereof, or a combination thereof wherein the derivative of amphetamine is l-amphetamine, methamphetamine, p-methoxyamphetamine, 3,4-methylenedioxyamphetamine, 2,3-methylenedioxyamphetamine, 3,4-methylenedioxymethamphetamine, 2,5-dimethoxy-4-methylamphetamine, 3,4,5-trimethoxyamphetamine, 2,4,5-trimethoxyamphetamine, 2,3,4-trimethoxyamphetamine, 2,3,5-trimethoxyamphetamine, 2,3,6-trimethoxyamphetamine, or 2,4,6-trimethoxyamphetamine.

In a further aspect, the present technology provides a composition for treating a human or animal patient having attention deficit disorder or attention deficit hyperactivity disorder, comprising a derivative of amphetamine chemically attached to a polar hydrophilic ligand, a salt thereof, or a combination thereof wherein the derivative of amphetamine is l-amphetamine.

In an additional aspect, the present technology provides a composition for treating a human or animal patient having attention deficit disorder or attention deficit hyperactivity disorder, comprising a derivative of amphetamine chemically attached to a polar hydrophilic ligand, a salt thereof, or a combination thereof wherein the salt thereof is an acefyllinate, 4-acetamidobenzoate, acetate, aceturate, adipate, aminosalicylate, ammonium, ascorbate, l-aspartate, benzoate, besylate, bicarbonate, borate, butyrate, calcium, camphocarbonate, camphorate, d-camsylate, l-camsylate, camsylate, carbonate, cholate, citrate, cypionate, decanoate, dichloroacetate, edentate, edisylate, estolate, esylate, ethyl sulfate, fumarate, furate, fusidate, galactarate (mucate), galacturonate, gallate, gentisate, gluceptate, gluconate, glucuronate, glutamate, glutarate, glycerophosphate, glycolate, heptanoate (enanthate), hexanoate, hippurate, hybenzate, hydrobromide/bromide, hydrochloride/chloride, hydroxide, hydroxybenzoate, iodide, isethionate, d-lactate, l-lactate, d,l-lactate, lactobionate, laurate, lithium, magnesium, malate, d,l-malate, maleate, malonate, mandelate, meso-tartrate, mesylate, methanesulfonate, methylsulfate, myristate, napadisilate, 2-napsylate, nicotinate, nitrate, octanoate, oleate, orotate, oxalate, palmitate, pamoate, phenylpropionate, phosphate, picrate, pivalate, potassium, propionate, pyrophosphate, salicylate, salicylsulfate, sodium, stearate, succinate, sulfate, sulfosalicylate, tannate, d-tartrate, kartrate, d,l-tartrate, terephthalate, thiocyanate, thiosalicylate, tosylate, tribrophenate, triflate, undecylenate, valerate, valproate, xinafoate, zinc, and mixtures thereof.

In an additional aspect, the present technology provides a composition for treating a human or animal patient having attention deficit disorder or attention deficit hyperactivity disorder, comprising a derivative of amphetamine chemically attached to a polar hydrophilic ligand, a salt thereof, or a combination thereof wherein the salt thereof is mesylate, a hydrochloride salt, a sulfate, an oxalate, a triflate, a citrate, a malate, a tartrate, a phosphate, a nitrate, a benzoate, or a mixture thereof.

Another aspect of the present technology provides a composition for treating a human or animal patient having attention deficit disorder or attention deficit hyperactivity disorder, comprising at least one conjugate, a salt of the conjugate, or a combination thereof; wherein the conjugate comprises amphetamine or a derivative thereof and homoarginine.

In a further aspect, the present technology provides a composition for treating a human or animal patient having attention deficit disorder or attention deficit hyperactivity disorder, comprising at least one conjugate, a salt of the conjugate, or a combination thereof, wherein the composition has a reduced pharmacological activity when administered by parenteral routes.

In an additional aspect, the present technology provides a composition for treating a human or animal patient having attention deficit disorder or attention deficit hyperactivity disorder, comprising at least one conjugate, a salt of the conjugate, or a combination thereof, wherein the composition is in the form of a tablet, a capsule, a caplet, a troche, a lozenge, an oral powder, a solution, a oral film, a thin strip, or a suspension.

In a further aspect, the present technology provides a composition for treating a human or animal patient having attention deficit disorder or attention deficit hyperactivity disorder, comprising at least one conjugate, a salt of the conjugate, or a combination thereof, wherein the composition is in the form or a chewable tablet, chewable troche, or chewable lozenge.

In another aspect, the present technology provides a composition for treating a human or animal patient having attention deficit disorder or attention deficit hyperactivity disorder, comprising at least one conjugate, a salt of the conjugate, or a combination thereof, wherein the conjugate, the salt of the conjugate, or the combination thereof is present in the amount of from about 1 mg to about 500 mg.

In an additional aspect, the present technology provides a composition for treating a human or animal patient having attention deficit disorder or attention deficit hyperactivity disorder, comprising at least one conjugate, a salt of the conjugate, or a combination thereof, wherein the conjugate, the salt of the conjugate, or the combination thereof is present in the amount of from about 5 mg to about 250 mg.

In another aspect, the present technology provides a composition for treating a human or animal patient having attention deficit disorder or attention deficit hyperactivity disorder, comprising at least one conjugate, a salt of the conjugate, or a combination thereof, wherein the conjugate, the salt of the conjugate, or the combination thereof is present in the amount of from about 10 mg to about 100 mg.

In a further aspect, the present technology provides a composition for treating a human or animal patient having attention deficit disorder or attention deficit hyperactivity disorder, comprising at least one conjugate, a salt of the conjugate, or a combination thereof, wherein the conjugate, the salt of the conjugate, or the combination thereof is in an amount sufficient to provide a therapeutically bioequivalent AUC when compared to amphetamine alone, but does not provide a $C_{max}$ spike.

In another aspect, the present technology provides a composition for treating a human or animal patient having attention deficit disorder or attention deficit hyperactivity disorder, comprising at least one conjugate, a salt of the conjugate, or a combination thereof, wherein the conjugate, the salt of the conjugate, or the combination thereof is in an amount sufficient to provide a therapeutically bioequivalent AUC when compared to amphetamine alone, but does not provide an equivalent $C_{max}$.

Another aspect of the present technology provides a method of treating a human or animal patient having attention deficit disorder or attention deficit hyperactivity disorder, comprising the step of orally administering to the patient a pharmaceutically effective amount of a composition comprising amphetamine chemically attached to a polar hydrophilic ligand, a salt thereof, or a combination thereof.

Other objects, advantages and embodiments of the invention are described below and will be obvious from this description and practice of the invention.

DETAILED DESCRIPTION OF THE INVENTION

Figure 1:
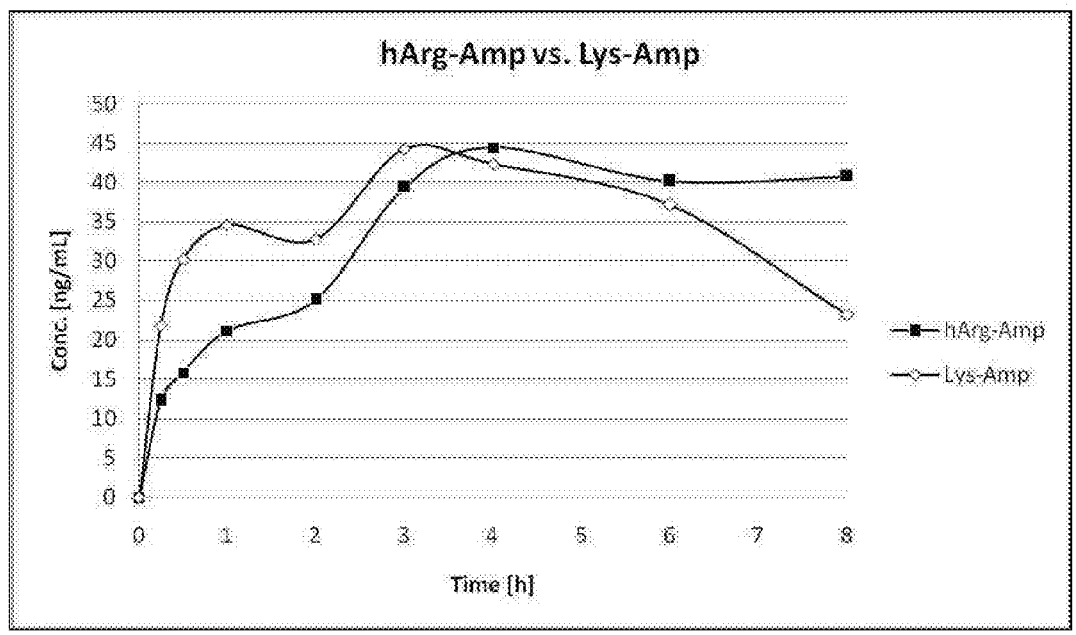
FIG. 1 compares mean plasma concentrations released from rats orally administered l-homoarginine-d-amphetamine or l-lysine-d-amphetamine.

The presently described technology relates to novel prodrugs/compositions of stimulants, including stimulants chemically attached to polar hydrophilic ligands, salts thereof, derivatives thereof, or combinations thereof. More specifically, the presently described technology is related, in some embodiments, to compositions comprising non-standard amino acid conjugates of amphetamine, salts thereof, derivatives thereof, or combinations thereof. Methods of making and using the prodrugs/compositions of the present technology are also disclosed.

Polar hydrophilic ligands suitable for the presently described technology can take a number of forms. These forms can be divided into several categories including non-standard amino acids, amino acid derivatives, amino acid precursors, amino alcohols, synthetic amino acid derivatives, natural substrates, and other hydrophilic groups or ligands. They can be in d-, l- or racemic form, or a mixture thereof along with a number of other possible enantiomeric/diastereomeric forms depending on the ligands. For example, the non-standard amino acid used to produce the stimulant prodrug of the present technology can be either d- or l-form amino acid, racemic amino acid, or a mixture thereof.

As used herein, a "non-standard" amino acid refers to an amino acid that is not one of the "standard" twenty amino acids. Non-standard amino acids may be derived from either natural or synthetic sources. Non-standard amino acids are non-essential and are not readily incorporated into proteins of natural origin. With the exception of selenocysteine and pyrrolysine, there are no known human genetic codons that are translated into non-standard amino acids. Non-standard amino acids may be metabolites of other amino acids or precursors in various metabolic pathways.

As used herein, an "amino acid derivative" is a chemically modified version of a naturally occurring amino acid (standard or non-standard). As used herein, an "amino acid precursor" refers to a molecule that can either chemically or metabolically breakdown into a naturally occurring amino acid (standard or non-standard). As used herein, a "synthetic amino acid" is an amino acid that is not naturally occurring. As used herein, an "amino alcohol" refers to a derivative of an amino acid (standard or non-standard, natural or synthetic) wherein the carboxylic acid group has been reduced to an alcohol.

As used herein, "amphetamine" shall mean any of the sympathomimetic phenethylamine derivatives which have central nervous system stimulant activity, such as but not limited to, amphetamine (α-methyl-phenethylamine), levoamphetamine, methamphetamine, p-methoxyamphetamine (PMA), methylenedioxyamphetamine, 3,4-methylenedioxyamphetamine (MDA), 2,3-methylenedioxyamphetamine, 2,5-dimethoxy-4-methylamphetamine (DOM), 3,4-methylenedioxy-methamphetamine (MDMA), 3,4,5-trimethoxyamphetamine (TMA), 2,4,5-trimethoxyamphetamine (TMA-2), 2,3,4-trimethoxyamphetamine (TMA-3), 2,3,5-trimethoxyamphetamine (TMA-4), 2,3,6-trimethoxyamphetamine (TMA-5), 2,4,6-trimethoxyamphetamine (TMA-6), and methylphenidate.

Please note that although the present technology sometimes may be described with a reference to amphetamine only, amphetamine is merely used as an example. It should be understood that any method or composition of the presently described technology is not limited to amphetamine.

As used herein, "in a manner inconsistent with the manufacturer's instructions" or similar expression is meant to include, but is not limited to, consuming amounts greater than amounts described on the label or ordered by a licensed physician, and/or altering by any means (e.g., crushing, breaking, melting, separating etc.) the dosage formulation such that the composition may be injected, inhaled or smoked.

As used herein, the phrases such as "decreased," "reduced," "diminished" or "lowered" is meant to include at least a 10% change in pharmacological activity with greater percentage changes being preferred for reduction in abuse potential and overdose potential. For instance, the change may also be greater than 25%, 35%, 45%, 55%, 65%, 75%, 85%, 95%, 96%, 97%, 98%, 99%, or increments therein.

Some abbreviations that may be used in the present application include: DCC=dicyclohexylcarbodiimide, NHS=N-hydroxysuccinimide, EtOAc=ethyl acetate, MsOH=methanesulfonic acid, EDCI=1-ethyl-3-(3-dimethylaminopropyl)carbodiimide, PyBrOP=bromo-tris-pyrrolidino phosphoniumhexafluorophosphate, NMM=N-methylmorpholine or 4-methylmorpholine, TEA=triethylamine, CDI=carbonyl diimidazole, IPAc=isopropyl acetate, DEA=diethylamine, BOP=(benzotriazol-1-yloxy)tris(dimethylamino)phosphonium hexafluorophosphate.

In accordance with some embodiments, the present technology provides stimulants such as amphetamine in a prodrug form. More specifically, the stimulant prodrug comprises at least one stimulant chemically attached to a polar hydrophilic ligand, a salt thereof, a derivative thereof, or a combination thereof.

In accordance with other embodiments, the amphetamine prodrug of the present technology comprises at least one non-standard amino acid covalently bonded or attached to amphetamine, which includes different forms or modified forms of sympathomimetic phenethylamine derivatives. The amino acid can be either the dextro-(d-) or levo- (l-) form of the amino acid, a racemic mixture of the amino acid, or a mixture thereof.

According to the presently described technology, polar hydrophilic molecules or ligands can be chemically (preferably covalently) attached to amphetamine (d-, l-, or racemic form or a mixture thereof) to produce novel polar, hydrophilic prodrugs of amphetamine. Other stimulants (including stimulant or stimulant-like drugs) can also be modified with these ligands. Some examples of other stimulants include adrafinil, modafinil, aminorex, benzylpiperazine, cathinone, chlorphentermine, chlobenzorex, cyclopentamine, diethylpropion, ephedrine, fenfluramine, 4-methyl-aminorex, methylone, methylphenidate, pemoline, phentermine, phenylephrine, propylhexadrine, pseudoephedrine, and synephrine. Metabolites and derivatives of these and other stimulants could also be modified with the same potential benefit. Examples of metabolites of amphetamine include p-hydroxyamphetamine and p-hydroxyephedrine.

In accordance with some embodiments of the presently described technology, the non-standard amino acid is attached to amphetamine to make the non-standard amino acid conjugate of amphetamine or salts thereof. Preferably, the non-standard amino acid is covalently attached to amphetamine through the C-terminus of the amino acid. The N-terminus or, when it is present, the side chain amino group of the amino acid may be in a free and unprotected state, or in the form of a salt thereof. Alternatively, in some embodiments, the non-standard amino acid can be attached to amphetamine through the N-terminus. Examples of salts of non-standard amino acid conjugates of amphetamine that can be formed and administered to patients in accordance with the presently described technology include, but are not limited to, acefyl-linate, 4-acetamidobenzoate, acetate, aceturate, adipate, aminosalicylate, ammonium, ascorbate, l-aspartate, benzoate, besylate, bicarbonate, borate, butyrate, calcium, camphocarbonate, camphorate, d-camsylate, l-camsylate, camsylate, carbonate, cholate, citrate, cypionate, decanoate, dichloroacetate, edentate, edisylate, estolate, esylate, ethyl sulfate, fumarate, furate, fusidate, galactarate (mucate), galacturonate, gallate, gentisate, gluceptate, gluconate, glucuronate, glutamate, glutarate, glycerophosphate, glycolate, heptanoate (enanthate), hexanoate, hippurate, hybenzate, hydrobromide/bromide, hydrochloride/chloride, hydroxide, hydroxybenzoate, iodide, isethionate, d-lactate, l-lactate, d,l-lactate, lactobionate, laurate, lithium, magnesium, malate, d,l-malate, maleate, malonate, mandelate, meso-tartrate, mesylate, methanesulfonate, methylsulfate, myristate, napadisilate, 2-napsylate, nicotinate, nitrate, octanoate, oleate, orotate, oxalate, palmitate, pamoate, phenylpropionate, phosphate, picrate, pivalate, potassium, propionate, pyrophosphate, salicylate, salicylsulfate, sodium, stearate, succinate, sulfate, sulfosalicylate, tannate, d-tartrate, l-tartrate, d,l-tartrate, terephthalate, thiocyanate, thiosalicylate, tosylate, tribrophenate, triflate, undecylenate, valerate, valproate, xinafoate, zinc, and mixtures thereof.

Examples of amphetamine derivatives of the present technology to which non-standard amino acids, including but not limited to homoarginine, can be chemically conjugated to are shown below in Tables 1 and 2.

TABLE 1

Amphetamine Derivatives

| Structure | Chemical Name |
|---|---|
| 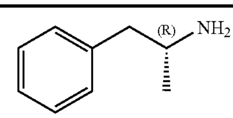 | levoamphetamine |
| 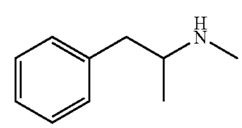 | methamphetamine |
| 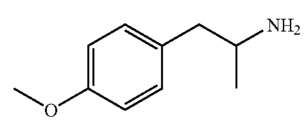 | p-methoxyamphetamine (PMA) |
| 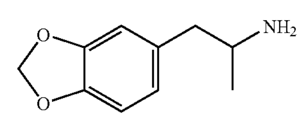 | 3,4-methylenedioxyamphetamine (MDA) |
| 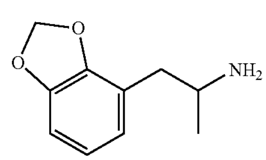 | 2,3-methylenedioxyamphetamine |
| 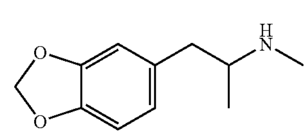 | 3,4-methylenedioxymethamphetamine (MDMA) |

TABLE 1-continued

Amphetamine Derivatives

| Structure | Chemical Name |
|---|---|
| 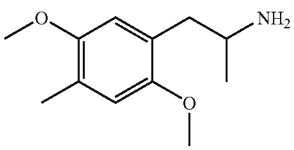 | 2,5-dimethoxy-4-methylamphetamine (DOM) |

TABLE 2

Trimethoxyamphetamine derivatives.

| Structure | Chemical Name |
|---|---|
| 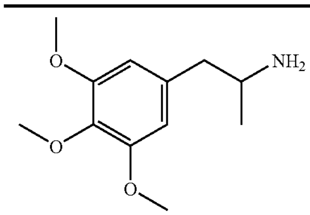 | 3,4,5-trimethoxyamphetamine (TMA) |
| 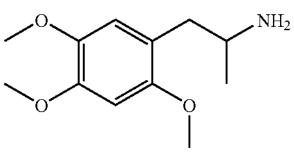 | 2,4,5-trimethoxyamphetamine (TMA-2) |
| 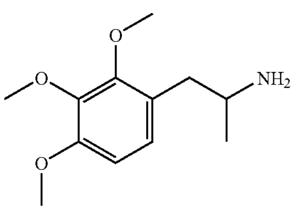 | 2,3,4-trimethoxyamphetamine (TMA-3) |
| 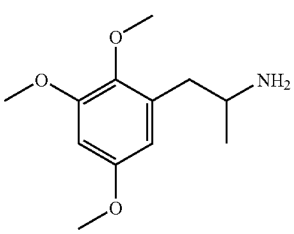 | 2,3,5-trimethoxyamphetamine (TMA-4) |
| 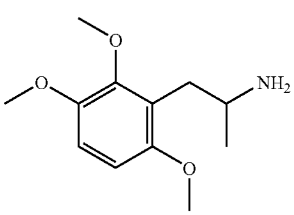 | 2,3,6-trimethoxyamphetamine (TMA-5) |
| 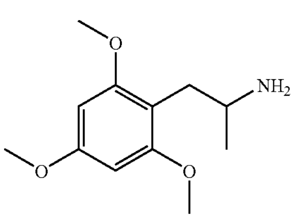 | 2,4,6-trimethoxyamphetamine (TMA-6) |

Examples of non-standard amino acids that are contemplated for the presently described technology include, but are not limited to: homoarginine, pyrrolysine, lanthionine, 2-aminoisobutyric acid, dehydroalanine, homocysteine, 2-oxoarginine, γ-aminobutyric acid (GABA), 4-amino butanoic acid, l,l-2,6-diaminopimelic acid, l-2-aminoadipate 6-semialdehyde, d-threo-2,4-diaminopentanoate, 2-amino-4-oxopentanoic acid, l-erythro-3,5-diaminohexanoic acid, (S)-5-amino-3-oxohexanoic acid, $N^6$-hydroxy-l-lysine, $N^6$-acyl-l-lysine, 5-aminovaleric acid, $N^6$-methyl-l-lysine, $N^6,N^6$-dimethyl-l-lysine, $N^6,N^6,N^6$-trimethyl-l-lysine, 3-hydroxy-$N^6,N^6,N^6$-trimethyl-l-lysine, 4-trimethylammoniobutanoic acid, 5-hydroxy-l-lysine, l-citrulline, 2-oxo-4-hydroxy-5-aminovalerate, pyrrole-2-carboxylate, l-erythro-4-hydroxyglutamic acid, trans-4-hydroxy-l-proline, 4-oxoproline, 3-sulfino-l-alanine, $O^3$-acetyl-l-serine, selenomethionine, selenocysteine, Se-methyl selenomethionine, Se-methyl selenocysteine, selenocystathionine, selenocysteine selenate, and cystathione.

In accordance with at least some embodiments, the polar hydrophilic ligands suitable for the present technology contain at least one of the following functional groups: hydroxyl, carboxylic acid, amine (primary or secondary), ketone or aldehyde, acetyl halide, phosphate, phosphonate, sulfate, sulfonate, sulfonyl, sulfonamide, and thiol. These functional groups can be chemically attached to amphetamine, for example, through the primary amine of amphetamine to form the following chemical linkages: carbamate, thiocarbamate, amide, urea, phosphoramidate, phosphonamidate, phosphoramide, sulfamate, sulfonamide, or thiourea. The final prodrug products of the present technology may be in a number of derivative forms such as salt forms depending on other functionality of the attached ligands and any deprotection steps that may or may not be necessary.

Salts of the stimulant chemically attached to the polar hydrophilic ligand that can be formed and utilized include, but are not limited to, acefyllinate, 4-acetamidobenzoate, acetate, aceturate, adipate, aminosalicylate, ammonium, ascorbate, l-aspartate, benzoate, besylate, bicarbonate, borate, butyrate, calcium, camphocarbonate, camphorate, d-camsylate, l-camsylate, camsylate, carbonate, cholate, citrate, cypionate, decanoate, dichloroacetate, edentate, edisylate, estolate, esylate, ethyl sulfate, fumarate, furate, fusidate, galactarate (mucate), galacturonate, gallate, gentisate, gluceptate, gluconate, glucuronate, glutamate, glutarate, glycerophosphate, glycolate, heptanoate (enanthate), hexanoate, hippurate, hybenzate, hydrobromide/bromide, hydrochloride/chloride, hydroxide, hydroxybenzoate, iodide, isethionate, d-lactate, l-lactate, d,l-lactate, lactobionate, laurate, lithium, magnesium, malate, d,l-malate, maleate, malonate, mandelate, meso-tartrate, mesylate, methanesulfonate, methylsulfate, myristate, napadisilate, 2-napsylate, nicotinate, nitrate, octanoate, oleate, orotate, oxalate, palmitate, pamoate, phenylpropionate, phosphate, picrate, pivalate, potassium, propionate, pyrophosphate, salicylate, salicylsulfate, sodium, stearate, succinate, sulfate, sulfosalicylate, tannate, d-tartrate, l-tartrate, d,l-tartrate, terephthalate, thiocyanate, thiosalicylate, tosylate, tribrophenate, triflate, undecylenate, valerate, valproate, xinafoate, zinc, and mixtures thereof. Further, in accordance with some embodiments, the salts may be required in multiple forms (e.g., di-, tri-, or tetra-). Other derivative forms such as free base, free acid, or neutral forms may also be prepared depending on the polar hydrophilic ligand used.

Examples of non-standard amino acids suitable for the presently described technology include homoarginine, citrulline, homocitrulline, hydroxyproline, 2-hydroxy-4-(methylthio)butanoic acid (HMB), γ-aminobutyric acid, taurine, glutathione, statine, homocysteine, selenomethionine, and combinations thereof. Structures of some non-standard amino acids are shown below.

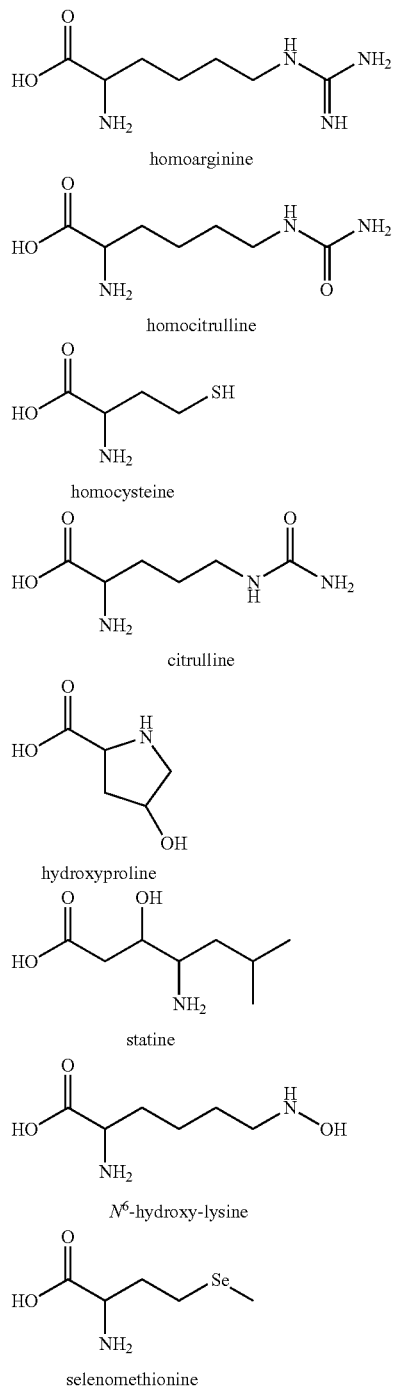

Examples of amino acids derivatives or precursors suitable in the presently described technology include isoserine, N-ω-nitro-arginine, N-ε,ε-dimethyl-lysine, buthionine, cysteic acid, ethionine, (2-amino ethyl)cysteine, cystathionine, 2-amino-3-ethyoxybutanoic acid, methylserine, O-ethyl-threonine, and combinations thereof. Structures of some amino acids derivatives or precursors for use in the practice of the present technology are provided below.

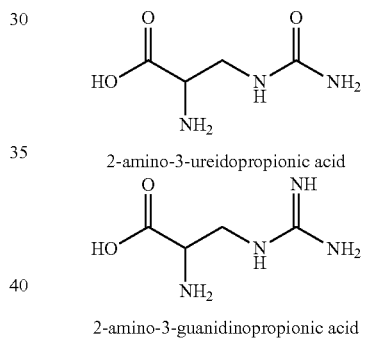

Examples of synthetic amino acids suitable for use in the presently described technology include 2-amino-3-guanidinopropionic acid, 2-amino-3-ureidopropioninc acid, 4-nitroanthranillic acid, and combinations thereof. Structures of some synthetic amino acids for use in the practice of the present technology are provided below.

2-amino-3-ureidopropionic acid 2-amino-3-guanidinopropionic acid

Examples of amino alcohols suitable for use in the presently described technology include alaminol, indano, norephedrine, asparaginol, aspartimol, glutamol, leucinol, methioninol, phenylalaminol, prolinol, tryptophanol, valinol, isoleucinol, argininol, serinol, tyrosinol, threoninol, cysteinol, lysinol, histidinol, and combinations thereof. Structures of some amino alcohols for use in the practice of the present technology are provided below.

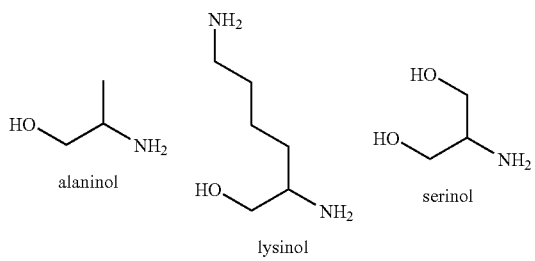

Other polar hydrophilic ligands that can be used to produce stimulant prodrugs of the present technology include natural substrates, and other hydrophilic groups. As used herein, "natural substrates" refer to polar molecules that are readily found in humans and can include essential or non-essential nutrients and biological components. Other hydrophilic groups or ligands include examples of compounds that occur in natural or are regarded as non-toxic and could not be readily classified in the other groupings.

Examples of some natural substrates suitable for use in the presently described technology include carnitine, tartaric acid, biotin, pantothenic acid and salts, choline, cystine dimer, lactic acid, niacin, riboflavin, and combinations thereof. Structures of some preferred natural substrates for use in the practice of the present technology are provided below.

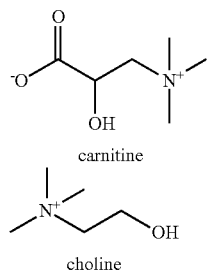
carnitine choline

Examples of other hydrophilic groups suitable for use in the presently described technology include t-butylated hydroxyanisole (BHA), propionic acid, sorbic acid, erythorbic acid, methyl paraben, propyl gallate, propyl paraben, thiodipropionic acid, propylene glycol, pyridoxine, adipic acid, malic acid, acetoin, N-butyric acid, vanillin, geraniol, methyl anthranilate, benzoin, benzyl alcohol, and combinations thereof. Structures of two representative hydrophilic groups for use in the practice of the present technology are provided below.

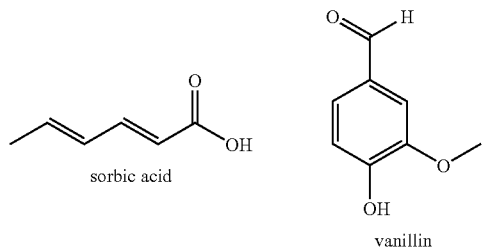
sorbic acid vanillin

Generally, to produce a stimulant prodrug of the present technology, a selected polar hydrophilic ligand (e.g., a commercially available non-standard amino acid or amino acid derivative) can be added to the stimulant (e.g. amphetamine) in dextro, levo or racemic forms. Depending on the polar hydrophilic ligand selected, one or more functional groups on the polar hydrophilic ligand may or may not need to be protected prior to coupling the ligand with the stimulant.

For example, to conjugate an amino acid with amphetamine, the one or more amino groups are preferably protected before the amino acid is reacted with amphetamine. Agents and methods for protecting amino groups in a reactant are known in the art. Examples of protecting groups that may be used to protect the amino groups include, but are not limited to, fluorenylmethoxycarbonyl (Fmoc), t-butylcarbonate (Boc), trifluoroacetate (TFA), acetate (Ac) and benzyloxycarbonyl (Z). After coupling with any standard coupling procedure, deprotection can occur with a variety of strong acids to give the corresponding salt form. Salt forms may also be switched by first free basing the product and then adding any acid. Neutral, free base or anionic salts may also be formed. Additional deprotection may be necessary in the case of some polar hydrophilic ligands such as homoarginine and any protected urea derivative. These deprotections usually occur under hydrogenation conditions.

For another example, coupling of carnitine (d-, l-, or racemic) to amphetamine may require protection of the hydroxyl group prior to coupling. In accordance with some embodiments, use of a silyl or benzoyl group to protect the hydroxyl group would be preferred. Deprotection of the silyl can occur in water or slightly acidic media. On the other hand, deprotection of benzoyl usually requires strong basic conditions such as in the presence of NaOMe.

More specifically, using a non-standard amino acid and amphetamine as an example, the non-standard amino acid can be attached to amphetamine to make an amino acid conjugate of amphetamine or salts thereof in accordance with the presently described technology. Preferably, the amino acid is covalently attached to amphetamine through the C-terminus of the amino acid. The N-terminus or the side chain amino group of the amino acid may be in a free and unprotected state, or in the form of a salt thereof. Alternatively, in some embodiments, the amino acid can be attached to amphetamine through the N-terminus. Examples of salts of amino acid conjugates of amphetamine that can be formed and administrated to patients in accordance with the presently described technology include, but are not limited to, acefyllinate, 4-acetamidobenzoate, acetate, aceturate, adipate, aminosalicylate, ammonium, ascorbate, l-aspartate, benzoate, besylate, bicarbonate, borate, butyrate, calcium, camphocarbonate, camphorate, d-camsylate, l-camsylate, camsylate, carbonate, cholate, citrate, cypionate, decanoate, dichloroacetate, edentate, edisylate, estolate, esylate, ethyl sulfate, fumarate, furate, fusidate, galactarate (mucate), galacturonate, gallate, gentisate, gluceptate, gluconate, glucuronate, glutamate, glutarate, glycerophosphate, glycolate, heptanoate (enanthate), hexanoate, hippurate, hybenzate, hydrobromide/bromide, hydrochloride/chloride, hydroxide, hydroxybenzoate, iodide, isethionate, d-lactate, l-lactate, d,l-lactate, lactobionate, laurate, lithium, magnesium, malate, d,l-malate, maleate, malonate, mandelate, meso-tartrate, mesylate, methanesulfonate, methylsulfate, myristate, napadisilate, 2-napsylate, nicotinate, nitrate, octanoate, oleate, orotate, oxalate, palmitate, pamoate, phenylpropionate, phosphate, picrate, pivalate, potassium, propionate, pyrophosphate, salicylate, salicylsulfate, sodium, stearate, succinate, sulfate, sulfosalicylate, tannate, d-tartrate, kartrate, d,l-tartrate, terephthalate, thiocyanate, thiosalicylate, tosylate, tribrophenate, triflate, undecylenate, valerate, valproate, xinafoate, zinc, and mixtures thereof.

To conjugate an amino acid of the present technology, including non-standard amino-acids, with amphetamine, the one or more amino groups are preferably protected using agents described above before the amino acid is reacted with amphetamine. The amino acid whose amino groups are protected can be referred to as an N-protected amino acid. One can either protect the amino groups in situ during the production process, or use commercially available N-protected amino acids directly. Preferably, the carboxylic acid group in the N-protected amino acid is activated by an acid activating agent (sometimes also called coupling reagent) to help the reaction of the N-protected amino acid with amphetamine. General information about the reaction of amino acids to form peptide bonds can be found in, for example, G. C. Barett, D. T. Elmare, Amino Acids and Peptides, page 151-156, Cambridge University Press, UK (1st edition, 1998); Jones, J., Amino Acid and Peptide Synthesis, pages 25-41, Oxford University Press, UK (2nd edition, 2002), which are incorporated herein by reference in their entirety.

One category of acid activating agents (coupling reagents) well known in the art are carbodiimides. Examples of carbodiimide acid activating agents include, but are not limited to, dicyclohexylcarbodiimide (DCC), 1-ethyl-3-(3'-dimethylaminopropyl)-carbodiimide (EDCI), and diisopropylcarbodiimide (DIPCDI). Examples of other coupling reagents that could be used include bromo-tris-pyrrolidino phosphonium-hexafluorophosphate, (benzotriazol-1-yloxy)-tris-(dimethylamino)-phosphonium hexafluorophosphate, $PCl_5/PhH$, $SOCl_2$, $N_2H_4$, 1-ethoxycarbonyl-2-ethoxy-1,2-dihydroquinoline, other phosphonium reagents, and uronium reagents. The use of appropriate acyl halide or anhydride is also contemplated.

The N-protected amino acid conjugate of amphetamine resulting from the reaction of the N-protected amino acid and amphetamine as described above can then be de- or un-protected with a strong acid to produce the corresponding final salt form of the amino acid conjugate of amphetamine.

Scheme 1 below outlines an exemplary route for the synthesis of a derivative of amphetamine chemically attached to homoarginine in accordance with the presently described technology. In this exemplary reaction scheme, a dihydrochloride salt form of homoarginine-amphetamine is produced. The procedure uses tert-butyloxycarbonyl (Boc) and nitro protected homoarginine (Boc-homoarginine($NO_2$)) as the starting material. In this exemplary reaction scheme, the coupling agent EDCI is added to Boc-homoarginine($NO_2$) in dimethylformamide (DMF). N-hydroxysuccinamide (NHS) is then added to the reaction mixture. A stable, yet still activated, succinimidyl ester of Boc-homoarginine($NO_2$) is formed. Amphetamine is then added to the resulting succinimidyl ester of Boc-homoarginine($NO_2$) to make the corresponding protected prodrug, Boc-homoarginine($NO_2$)-amphetamine. This protected prodrug can be de- or un-protected using hydrogenation followed by a strong acid such as methanesulfonic acid (MsOH) or hydrochloric acid to produce the prodrug of amphetamine, which is a dihydrochloride salt of homoarginine-amphetamine in this exemplary reaction scheme.

Scheme 1

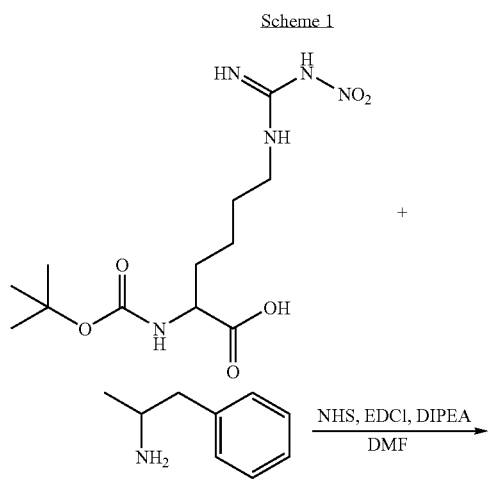

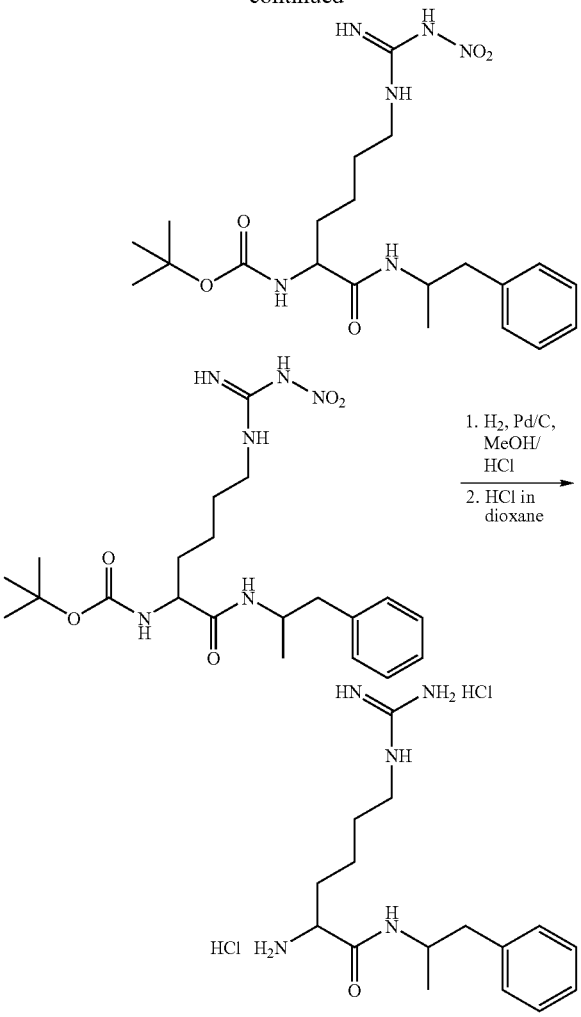

The preparation of hArg-Amp required extensive modifications to previously published methods and syntheses. First, Boc-hArg($NO_2$)—OH required use of DMF to solubilize the material prior to reaction. Second, formation of the free base of amphetamine was performed in situ and was not isolated. Also, the formation of the activated ester was performed in situ with the addition reaction following in the same reaction vessel. Homoarginine is different from many other standard and non-standard amino acids in that it requires a separate step of deprotection to remove the nitro group from the side chain. Failure to adequately protect homoarginine can lead to undesirable products that do not perform in vivo with respect to the desired therapeutic outcomes discussed herein.

Examples of other solvents that can be used in the presently described technology include, but are not limited to, isopropyl acetate (IPAc), acetone, and dichloromethane (DCM), dimethylformamide (DMF), ethyl acetate, chloroform, dimethyl sulfoxide, dioxane, diethyl ether, methyl t-butyl ether, hexanes, heptane, methanol, ethanol, isopropanol, and butanol. A mixture of different solvents can also be used. Co-bases such as tertiary amines may or may not be added in the coupling reaction of the presently described technology. Example of suitable co-bases include, but are not limited to 4-methylmorpholine (NMM), triethylamine (TEA), ammonia or any tertiary amine base.

The amphetamine to be chemically attached to polar hydrophilic ligands of the presently described technology can be in d-form, l-form, or racemic form, or can be a mixture thereof. In accordance with some embodiments of the presently described technology, d-amphetamine (dextroamphetamine) and a non-standard amino acid with a know toxicity profile are preferably used to make an amphetamine prodrug. Other preferred polar hydrophilic ligands to form d-amphetamine prodrugs include, for example, l-carnitine, l-lysinol, or choline. In accordance with some other embodiments, the prodrugs of d-amphetamine can be used in combination with a prodrug of l-amphetamine or l-amphetamine itself.

Scheme 2 below outlines an exemplary route for the synthesis of a derivative of amphetamine chemically attached to selenomethionine in accordance with the presently described technology. The amphetamine prodrug produced here is in a sulfate salt form.

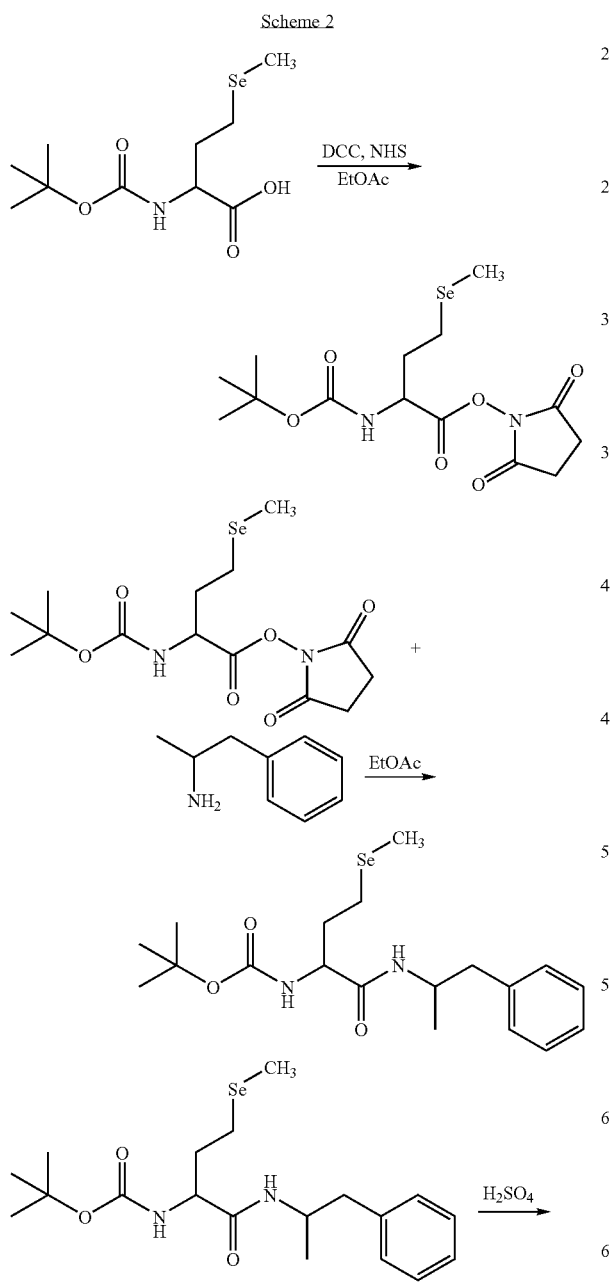

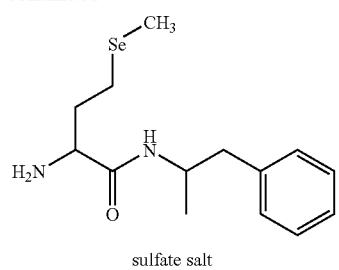

sulfate salt

Scheme 3 below outlines an exemplary route for the synthesis of a derivative of amphetamine chemically attached to statine in accordance with the presently described technology. The amphetamine prodrug produced here is in an HCl salt form.

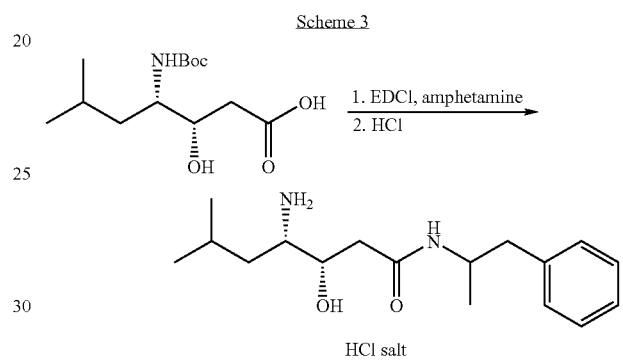

HCl salt

Scheme 4 below outlines an exemplary route for the synthesis of a derivative of amphetamine chemically attached to isoserine in accordance with the presently described technology. The amphetamine prodrug produced here is in an MsOH salt form.

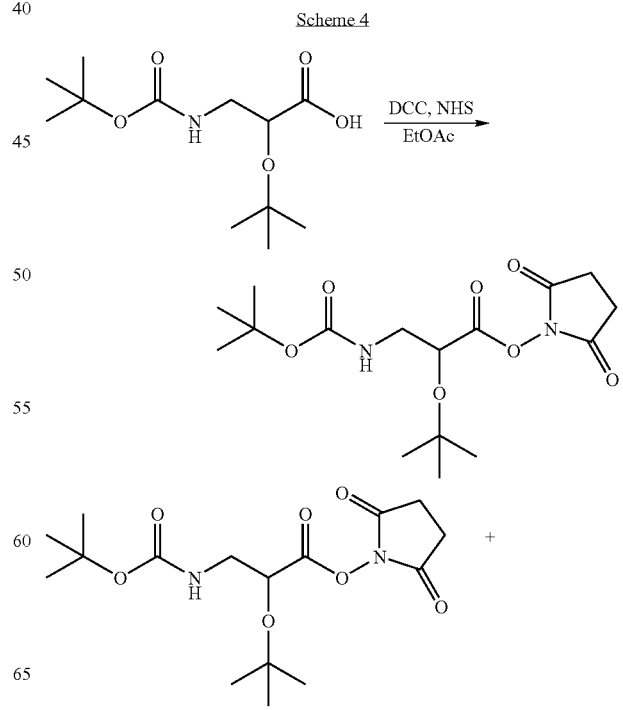

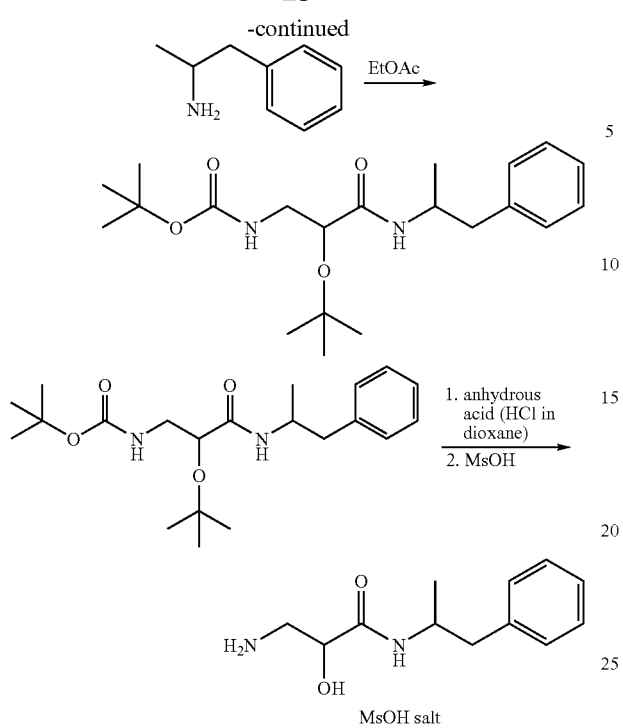

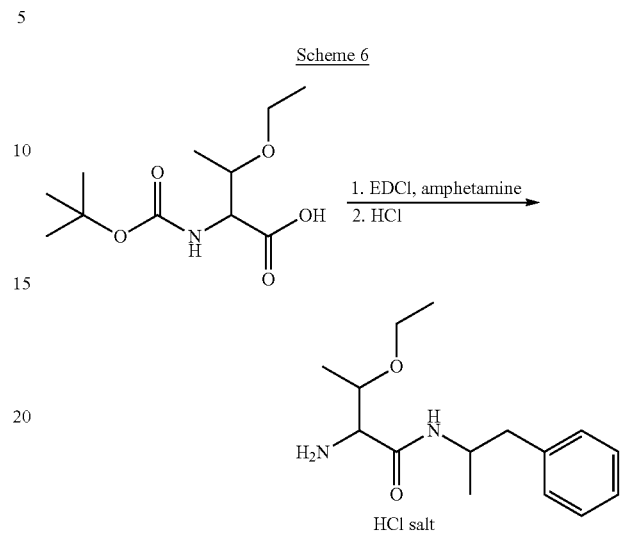

O-ethyl-threonine in accordance with the presently described technology. The amphetamine prodrug produced here is in an HCl salt form.

Scheme 5 below outlines an exemplary route for the synthesis of a derivative of amphetamine chemically attached to cystathionine in accordance with the presently described technology. The amphetamine prodrug produced here is in an HCl salt form.

Scheme 7 below outlines an exemplary route for the synthesis of a derivative of amphetamine chemically attached to 2-amino-3-guanidinopropionic acid in accordance with the presently described technology. The amphetamine prodrug produced here is in an MsOH salt form.

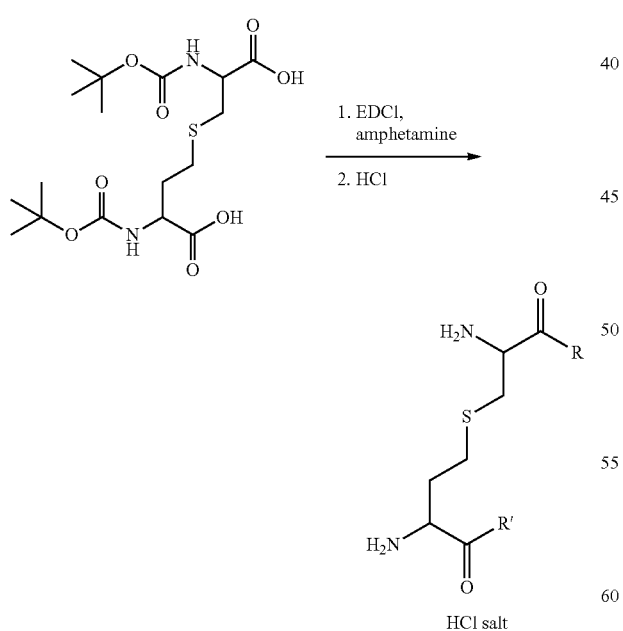

R = OH or amphetamine
R' = OH or amphetamine

Scheme 6 below outlines an exemplary route for the synthesis of a derivative of amphetamine chemically attached to

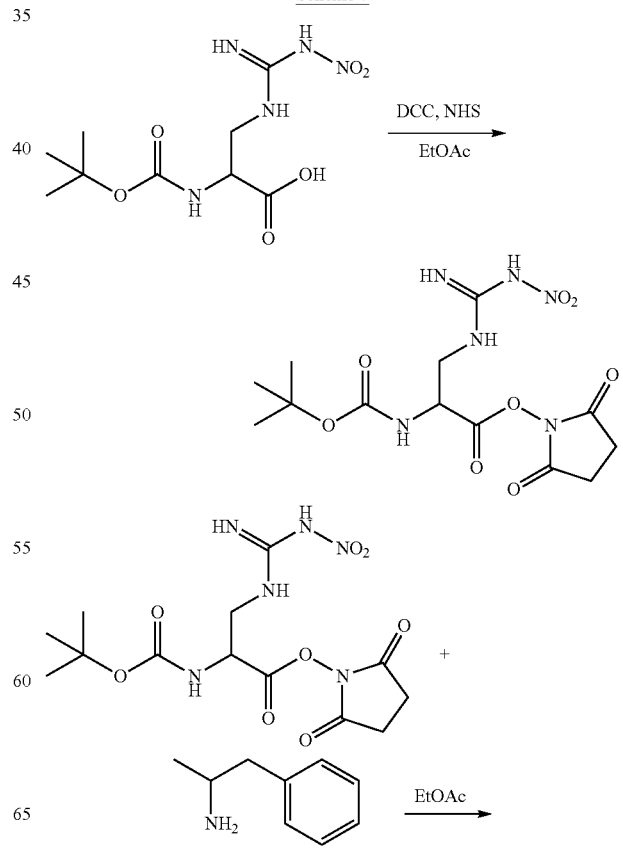

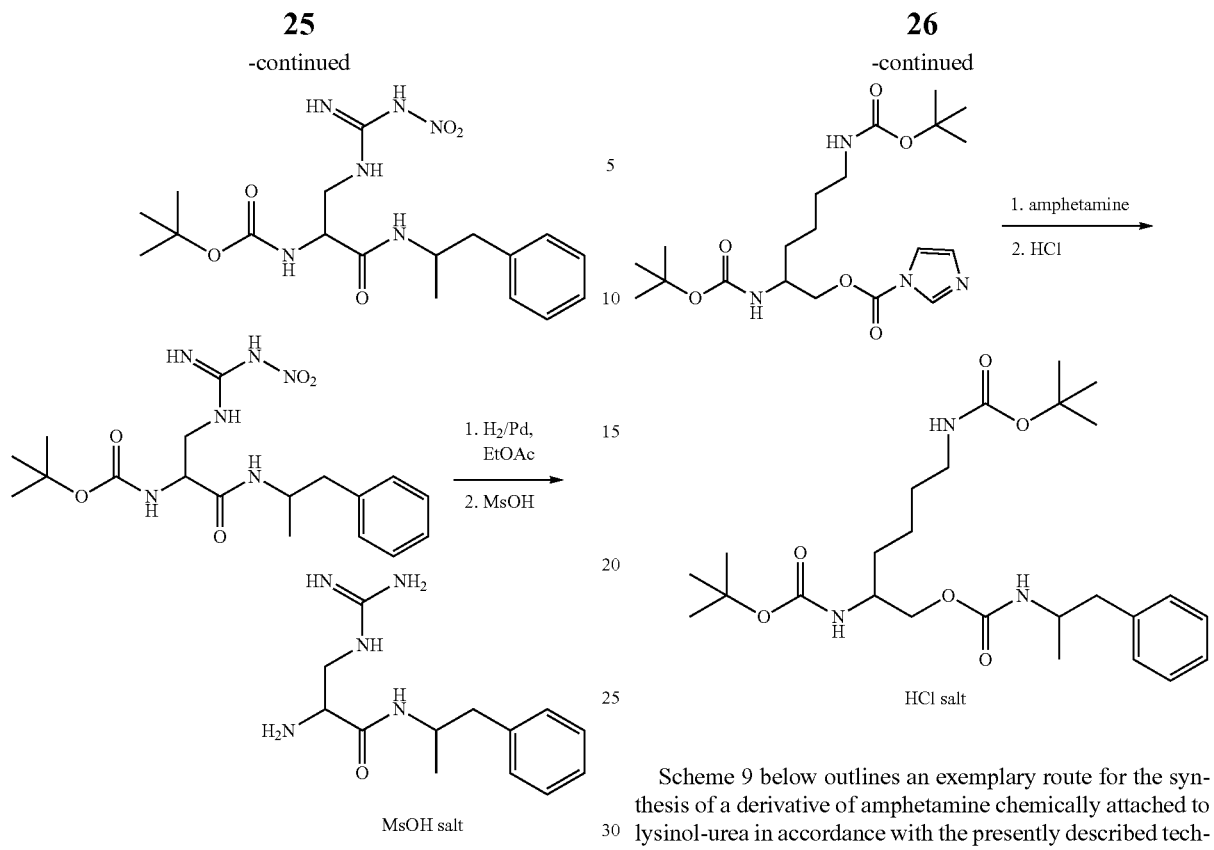

Scheme 9 below outlines an exemplary route for the synthesis of a derivative of amphetamine chemically attached to lysinol-urea in accordance with the presently described technology.

Scheme 8 below outlines an exemplary route for the synthesis of a derivative of amphetamine chemically attached to lysinol-carbamate in accordance with the presently described technology. The amphetamine prodrug produced here is in an HCl salt form.

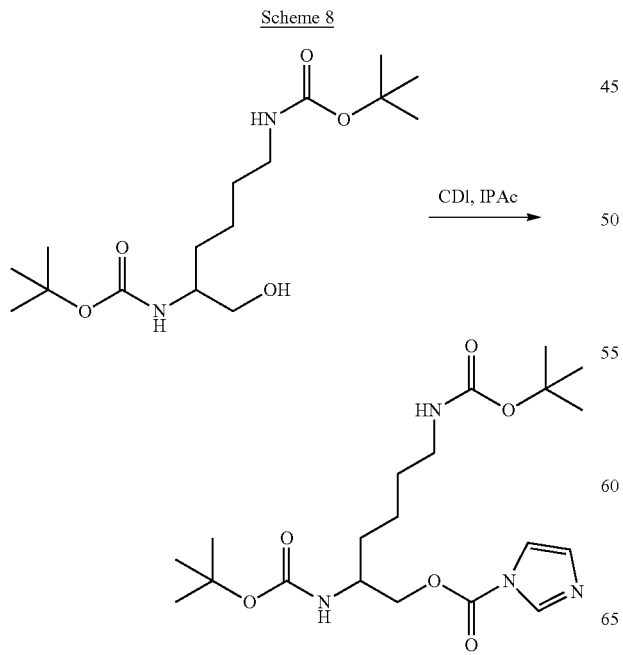

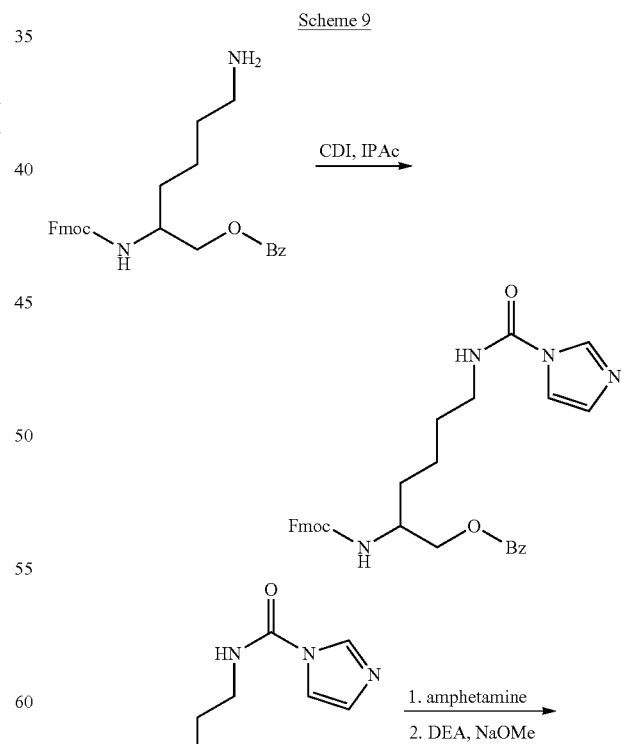

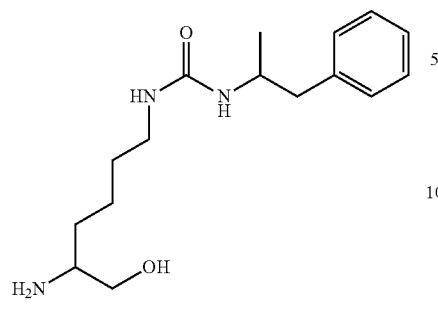

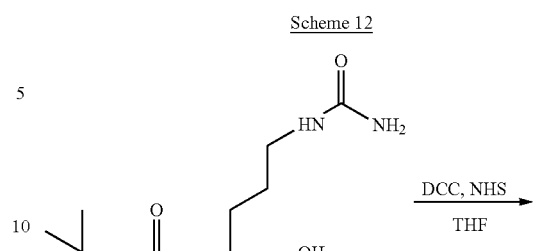

Scheme 10 below outlines an exemplary route for the synthesis of a derivative of amphetamine chemically attached to carnitine in accordance with the presently described technology.

Scheme 10

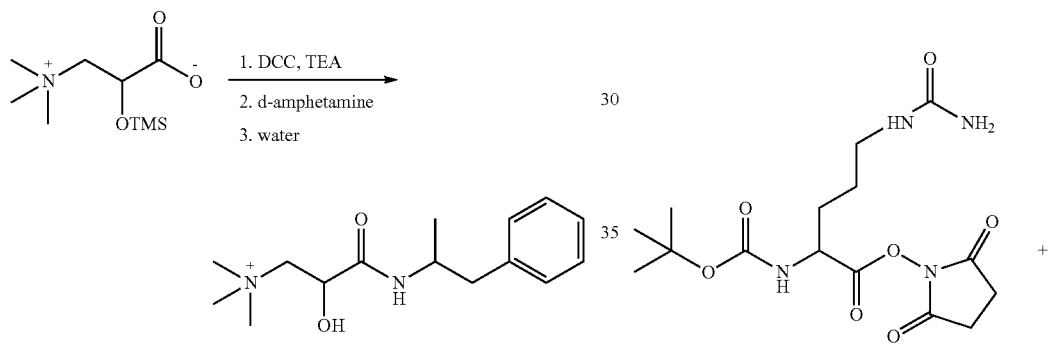

Scheme 11 below outlines an exemplary route for the synthesis of a derivative of amphetamine chemically attached to choline in accordance with the presently described technology.

Scheme 11

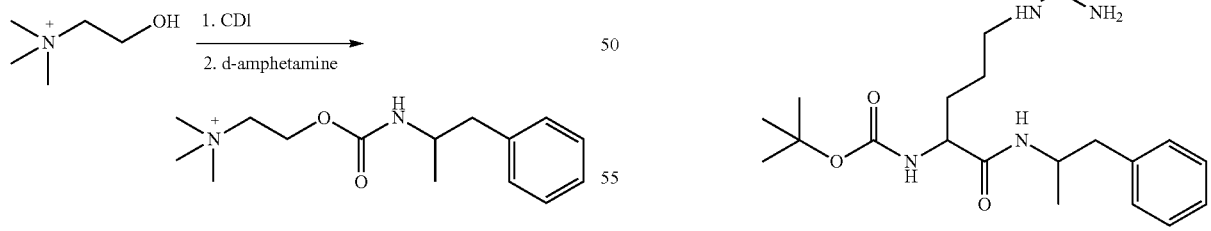

In some other preferred embodiments of the present technology, l-citrulline-d-amphetamine hydrochloride (Cit-Amp) can be synthesized as shown in reaction Scheme 12 below in three overall steps. The first step involves the activation of Boc-Cit-OH to form an activated ester using DCC and NHS followed by the addition of d-amphetamine to produce the protected Boc-Cit-Amp. Deprotection using 4N HCl in dioxane gives the corresponding hydrochloride salt.

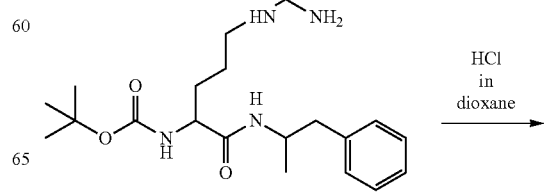

-continued

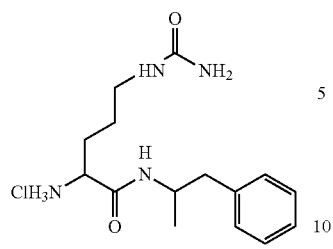

Another example of the preparation of homoarginine conjugates of amphetamine derivatives of the present technology is shown in the general pathway of Scheme 13.

Scheme 15 provides an exemplary route for the synthesis of a methylenedioxyamphetamine derivative (example shows 3,4-methylenedioxyamphetamine) chemically attached to homoarginine.

Scheme 13

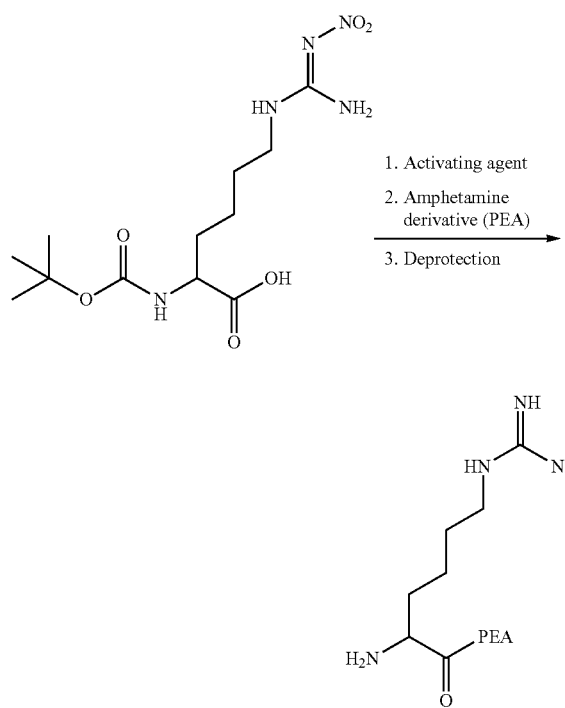

Scheme 15

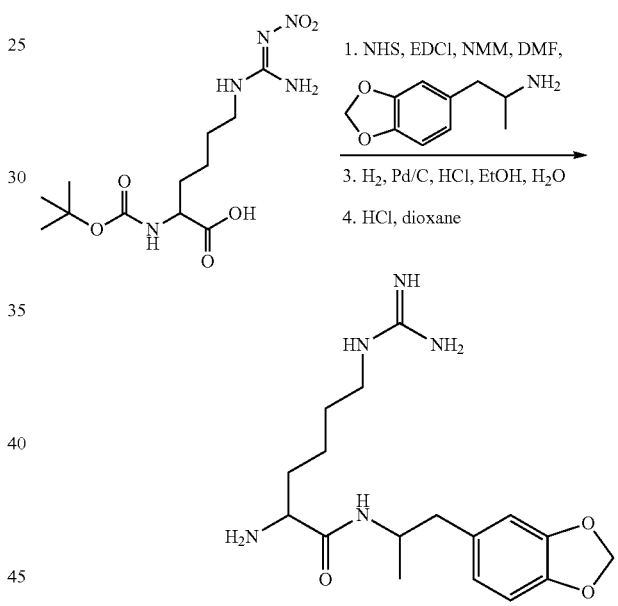

Scheme 14 provides an exemplary route for the synthesis of p-methoxyamphetamine (PMA) chemically attached to homoarginine.

Scheme 16 provides an exemplary route for the synthesis of 2,5-dimethoxy-4-methylamphetamine (DOM) chemically attached to homoarginine.

Scheme 14

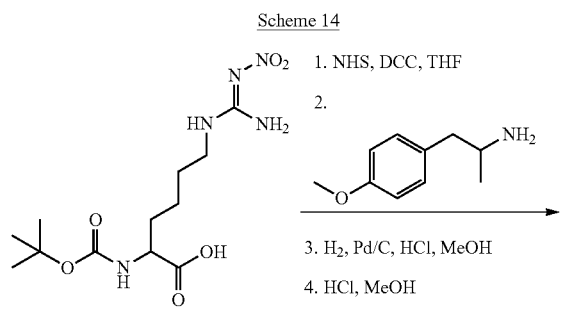

Scheme 16

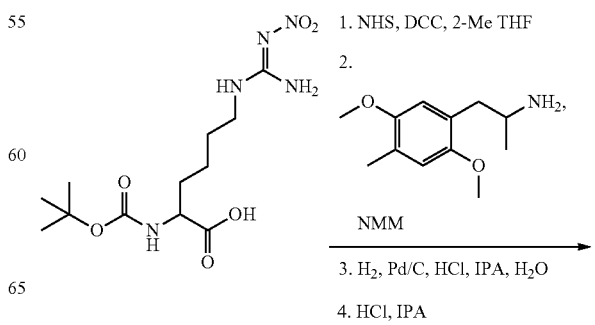

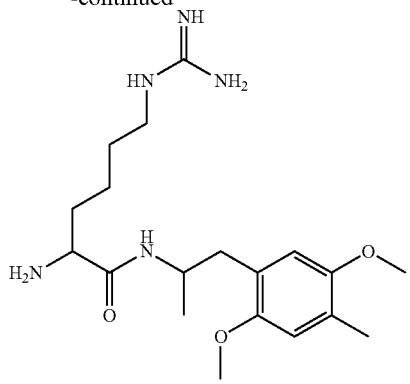

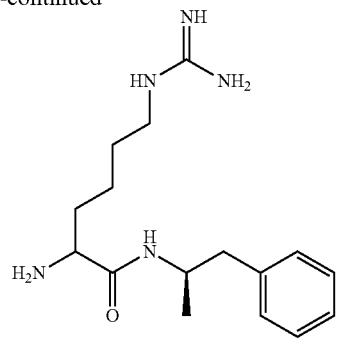

Scheme 17 provides an exemplary route for the synthesis of a trimethoxyamphetamine derivative (example shows 3,4,5-trimethoxyamphetamine) chemically attached to homoarginine.

Scheme 17

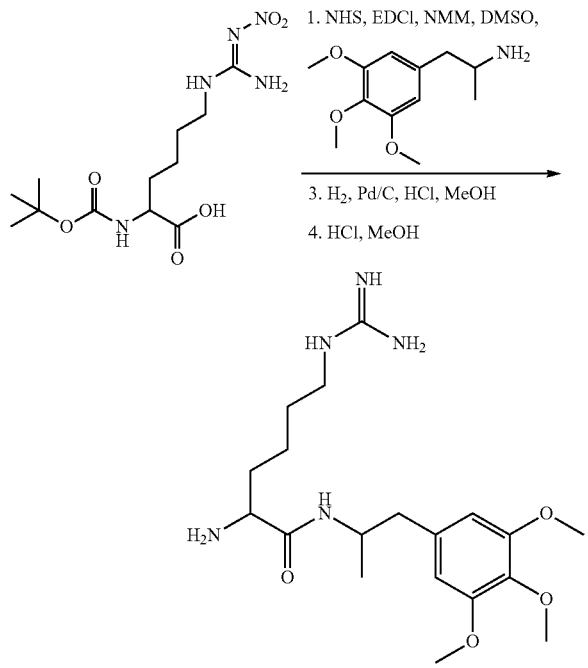

Scheme 18 provides an exemplary route for the synthesis of levoamphetamine chemically attached to homoarginine.

Scheme 18

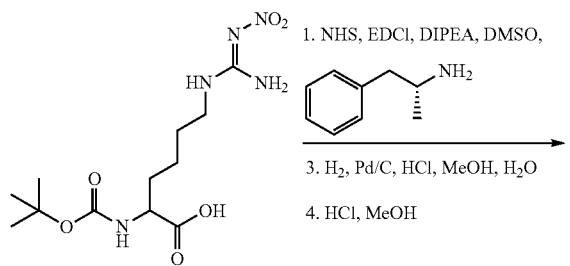

At least some compounds of the present technology, including polar, hydrophilic stimulant prodrugs, have no or a substantially decreased pharmacological activity when administered through alternative routes of administration including, but not limited to, injection or intranasal. However, they remain orally bioavailable. The bioavailability can be a result of the hydrolysis of the covalent linkage following oral administration. Hydrolysis of a chemical linkage is time-dependent, thereby allowing amphetamine and other metabolites such as p-hydroxyamphetamine and p-hydroxyephedrine or another stimulant to become available in its active form over an extended period of time.

Therefore, the prodrug compounds of the present technology can release amphetamine or another stimulant over an extended period and provide a therapeutically area under the curve (AUC) when compared to free amphetamine or another stimulant (including other controlled release forms of amphetamine such as Adderall XR® or Vyvanse™), with little or no spike in maximum plasma concentration ($C_{max}$) or equivalent $C_{max}$. Not wanting to be bound by any particular theory, it is believed that since non-standard amino acids and the other suitable polar hydrophilic ligands are used to produce the prodrugs, the in vivo breakdown of the prodrugs by enzymes would occur at a slower rate than, for example, when a standard amino acid is used to conjugate the stimulants. This will allow the prodrugs of the present technology to release amphetamine or other stimulants slowly and, preferably, only under in vivo conditions.

As a person of ordinary skill in the art will understand, drug products are considered pharmaceutical equivalents if they contain the same active ingredient(s), are of the same dosage form, route of administration and are identical in strength or concentration. Pharmaceutically equivalent drug products are formulated to contain the same amount of active ingredient in the same dosage form and to meet the same or compendial or other applicable standards (i.e., strength, quality, purity, and identity), but they may differ in characteristics such as shape, scoring configuration, release mechanisms, packaging, excipients (including colors, flavors, preservatives), expiration time, and, with certain limits, labeling. Drug products are considered to be therapeutic equivalents only if they are pharmaceutical equivalents and if they can be expected to have the same clinical effect and safety profile when administered to patients under the conditions specified in the labeling. The term "bioequivalent," on the other hand, describes pharmaceutical equivalent or pharmaceutical alternative products that display comparable bioavailability when studied under similar experimental conditions.

Standard amino acids such as lysine or glutamic acid are not contemplated for the presently described technology. Because standard amino acids are essential parts of all dietary requirements, it would be expected that the prodrug of the present technology conjugated with a standard amino acid would be released at a faster rate. By using non-standard amino acids, synthetic amino acids, amino acid derivatives or precursors, or other polar hydrophilic ligands of the presently described technology, the release rate of amphetamine or another stimulant will be reduced due to the difference in overall digestion rate of the stimulant prodrug.

Once produced, the prodrug of amphetamine (or another stimulant) of the present technology can be administered through oral routes of delivery and once administered will release the stimulant under digestive conditions. Due to the hydrophilic and polar nature of the prodrug and the slow rate of hydrolysis of the chemical linkage as described above, should high levels of drug be administered either accidentally or intentionally, the prodrug will be cleared by metabolic and/or excretory pathways prior to releasing large amounts of the stimulant. Also, release of amphetamine (or another stimulant) over an extended period should alleviate or diminish drug induced side-effects that can limit or terminate amphetamine therapy. These side effects include increase in the heart and respiration rates, increased blood pressure, dilation of the pupils of the eyes, and decreased appetite. Other side effects include anxiety, blurred vision, sleeplessness, and dizziness. Also, amphetamines and other stimulants are power psychostimulants and are prone to substance abuse.

Substance abuse of stimulants is often characterized by an escalation of events. First, a substantial "rush" or high may be obtained from increasing oral dosages. Due to the properties of these polar, hydrophilic prodrugs, these potential routes for abuse can be mitigated via the polar nature of the prodrug. That is, once administered at higher than therapeutic levels, the body will excrete any remaining prodrug without breakdown into amphetamine. After oral amounts exceed an attainable amount, other routes can be explored including smoking, snorting, or injection. In accordance with the presently described technology, release of amphetamine or another stimulant would only occur under desired physiological conditions. Preferably, non-oral routes of administration (e.g., intranasal or intravenous) do not break the prodrug down to any appreciable extent. Also preferably, external means (chemical, enzymatic or other) will not break the prodrug down to any appreciable extent either. The breakdown ratio of the prodrug that can be achieved through external means is preferably less than about 50%, alternatively less than about 25%, alternatively less than about 20%, alternatively less than about 10%.

The presently described technology utilizes covalent modification of amphetamine by a non-standard amino acid, an amino acid derivative or any polar hydrophilic group to decrease its potential for causing behavioral deterioration or the rebound effect. It is believed that since the amphetamine is covalently modified to form the polar hydrophilic conjugate of the present technology and releases slowly over the entire length of the day, little or no rebound effect can occur due to the slow continuous release of the active ingredient/drug/therapeutic component.

Compounds, compositions and methods of the presently described technology are also believed to provide reduced potential for rebound, reduced potential for abuse or addiction, and/or improve amphetamine's stimulant related toxicities. By limiting the blood level spike, doses are kept at levels required for a clinically significant effect without the unnecessary levels administered with other therapies. It is widely held that these spikes in blood levels can lead to cardiovascular toxicity in the form of higher blood pressure and rapid heart rate in addition to the euphoria encountered in drug abuse. Also, with a full day therapy, the risk of re-dosing is lowered, thus preventing additional toxicities or drug abuse issues.

The polar, hydrophilic prodrugs of stimulants, including, but not limited to, amphetamine prodrugs, of the presently described technology could be used for any condition requiring the stimulation of the central nervous system (CNS). These conditions include, for example, attention deficit hyperactivity disorder (ADHD), attention deficit disorder (ADD), obesity, narcolepsy, appetite suppressant, depression, anxiety, withdrawals (e.g., alcohol withdrawals or drug withdrawals), and wakefulness. Some stimulants such as amphetamine have also demonstrated usefulness in treating stimulant (e.g., cocaine, methamphetamine) abuse and addiction. Amphetamine stimulants have also been used extensively to improve battle field alertness and to combat fatigue.

Therefore, in accordance with some embodiments, the presently described technology provides stimulant compositions comprising at least one polar, hydrophilic stimulant prodrug of the present technology.

In accordance with some other embodiments, the presently described technology provides amphetamine compositions comprising at least one amphetamine prodrug of the present technology.

One embodiment is a composition that can prevent behavioral deterioration of amphetamine dosing comprising at least one polar hydrophilic conjugate of amphetamine.

Another embodiment is a composition that can prevent behavioral deterioration of amphetamine dosing comprising at least one non-standard amino acid conjugate of amphetamine.

Another embodiment is a composition for safely delivering a stimulant, comprising a therapeutically effective amount of at least one polar, hydrophilic prodrug of the stimulant of the present technology wherein the polar hydrophilic moiety can reduce the rate of absorption of the stimulant as compared to delivering the unconjugated stimulant or the stimulant conjugated to a standard amino acid, for example.

Another embodiment is a composition for safely delivering amphetamine, comprising a therapeutically effective amount of at least one non-standard amino acid conjugate of amphetamine wherein the non-standard amino acid moiety can reduce the rate of absorption of the amphetamine as compared to delivering the unconjugated amphetamine or amphetamine conjugated to a standard amino acid.

Another embodiment of the present technology is a composition that can reduce amphetamine toxicity, comprising at least one polar hydrophilic prodrug of amphetamine wherein the non-standard amino acid moiety can release amphetamine over the entire course of a day providing a limited behavioral deterioration effect.

Another embodiment of the present technology is a composition that can reduce amphetamine toxicity, comprising at least one non-standard amino acid conjugate of amphetamine wherein the non-standard amino acid moiety can release amphetamine over the entire course of a day providing a limited behavioral deterioration effect.

Another embodiment of the present technology is a composition that can reduce amphetamine toxicity, comprising at least one polar, hydrophilic prodrug of amphetamine of the present technology wherein the polar hydrophilic moiety can provide a plasma release curve which does not increase above amphetamine's toxicity level when given at doses exceeding those within the therapeutic range of amphetamine.

Another embodiment of the present technology is a composition that can reduce amphetamine toxicity, comprising at least one non-standard amino acid conjugate of amphetamine wherein the non-standard amino acid moiety can provide a plasma release curve which does not increase above amphetamine's therapeutic level and does not cause blood level spiking.

Another embodiment of the present technology is a composition that can reduce bioavailability of amphetamine, comprising at least one polar, hydrophilic prodrug of amphetamine of the present technology wherein the amphetamine prodrug can maintain a steady-state plasma release curve which can provide a therapeutically effective bioavailability but prevent spiking or increased plasma concentrations compared to unconjugated amphetamine or amphetamine conjugated with a standard amino acid when given at doses exceeding those within the therapeutic range of amphetamine.

Another embodiment of the present technology is a composition that can reduce bioavailability of amphetamine or prevent a toxic release profile in a patient, comprising at least one non-standard amino acid conjugate of amphetamine wherein the non-standard amino acid conjugate of amphetamine can maintain a steady-state plasma release curve which can provide a therapeutically effective bioavailability but prevent spiking or increased plasma concentrations compared to unconjugated amphetamine or amphetamine conjugated with a standard amino acid.

Another embodiment of the present technology is a composition comprising at least one polar, hydrophilic prodrug of amphetamine of the present technology that can prevent a $C_{max}$ or equivalent $C_{max}$ spike for amphetamine when taken by means other than orally while still providing a therapeutically effective bioavailability curve if taken orally.

Another embodiment of the present technology is a composition comprising at least one non-standard amino acid conjugate of amphetamine that can prevent a $C_{max}$ or equivalent $C_{max}$ spike for amphetamine.

Another embodiment of the present technology is a composition comprising at least one non-standard amino acid conjugate of amphetamine that can prevent a $C_{max}$ or equivalent $C_{max}$ spike for amphetamine when taken by means other than orally while still providing a therapeutically effective bioavailability curve if taken orally.

Another embodiment of the present technology is a composition that can prevent a toxic release profile in a patient comprising at least one polar, hydrophilic prodrug of amphetamine of the present technology wherein the amphetamine prodrug can maintain a steady-state plasma release curve which provides a therapeutically effective bioavailability but prevents spiking or increased plasma concentrations compared to unconjugated amphetamine or amphetamine conjugated with a naturally occurring and standard amino acid.

One or more embodiments of the present technology provide stimulant such as amphetamine compositions which allow the stimulant to be therapeutically effective when delivered at the proper dosage but reduces the rate of absorption or extent of bioavailability of the stimulant when given at doses exceeding those within the therapeutic range of the stimulant. One or more embodiments of the present technology also provide stimulant compositions wherein the polar hydrophilic moiety increases the rate of clearance of the stimulant when given at doses exceeding those within the therapeutic range of the stimulant.

In one or more embodiments, the stimulant compositions of the present technology have substantially lower toxicity compared to unconjugated stimulant or the stimulant conjugated with a standard amino acid. In one or more embodiments, the stimulant compositions of the present technology can reduce or eliminate the possibility of overdose by oral administration. In one or more embodiments, the stimulant compositions of the present technology can reduce or eliminate the possibility of overdose by intranasal administration. In one or more embodiments, the stimulant compositions of the present technology can reduce or eliminate the possibility of overdose by injection. In one or more embodiments, the stimulant compositions of the present technology can reduce or eliminate the possibility of overdose by inhalation.

In one or more embodiments, the polar, hydrophilic prodrugs of stimulants, such as non-standard amino acid conjugates of amphetamine, of the present technology may further comprise a polymer blend which comprises a hydrophilic polymer and/or a water-insoluble polymer. The polymers may be used according to industry standards to further enhance the sustained release/abuse resistant properties of the stimulant prodrug of the present technology without reducing the abuse resistance. For instance, a composition might include: about 70% to about 100% stimulant prodrug of the present technology by weight, from about 0.01% to about 10% of a hydrophilic polymer (e.g. hydroxypropyl methylcellulose), from about 0.01% to about 2.5% of a water-insoluble polymer (e.g. acrylic resin), from about 0.01% to about 1.5% of additives (e.g. magnesium stearate), and from about 0.01% to about 1% colorant by weight.

Hydrophilic polymers suitable for use in the sustained release formulations include one or more natural or partially or totally synthetic hydrophilic gums such as acacia, gum tragacanth, locust bean gum, guar gum, or karaya gum, modified cellulosic substances such as methylcellulose, hydroxymethylcellulose, hydroxypropyl methylcellulose, hydroxypropyl cellulose, hydroxyethylcellulose, carboxymethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art, or a combination of such polymers. These hydrophilic polymers gel and would dissolve slowly in aqueous acidic media thereby allowing the stimulant prodrug to diffuse from the gel in the stomach. When the gel reaches the intestines it would dissolve in controlled quantities in the higher pH medium to allow further sustained release. Preferred hydrophilic polymers are the hydroxypropyl methylcelluloses such as those manufactured by The Dow Chemical Company and known as Methocel ethers, such as Methocel E1OM.

Other formulations according to one or more embodiments of the present technology may further comprise pharmaceutical additives including, but not limited to, lubricants such as magnesium stearate, calcium stearate, zinc stearate, powdered stearic acid, hydrogenated vegetable oils, talc, polyethylene glycol, and mineral oil; colorants such as Emerald Green Lake, FD&C Red No. 40, FD&C Yellow No. 6, D&C Yellow No. 10, or FD&C Blue No. 1 and other various certified color additives (See 21 CFR, Part 74); binders such as sucrose, lactose, gelatin, starch paste, acacia, tragacanth, povidone, polyethylene glycol, Pullulan and corn syrup; glidants such as colloidal silicon dioxide and talc; surface active agents such as sodium lauryl sulfate, dioctyl sodium sulfosuccinate, triethanolamine, polyoxyethylene sorbitan, poloxalkol, and quaternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. In one preferred embodiment, a sustained release formulation of the present technology further comprises magnesium stearate and Emerald Green Lake.

The stimulant compositions, such as amphetamine compositions, of the present technology, which comprises at least one polar, hydrophilic stimulant prodrug of the present technology, can be further formulated with excipients, and may be manufactured according to any appropriate method known to those of skill in the art of pharmaceutical manufacture. For instance, the stimulant prodrug and a hydrophilic polymer may be mixed in a mixer with an aliquot of water to form a wet granulation. The granulation may be dried to obtain hydrophilic polymer encapsulated granules of the stimulant prodrug. The resulting granulation may be milled, screened, then blended with various pharmaceutical additives such as, for example, water insoluble polymers, and/or additional hydrophilic polymers. The formulation may then be tableted and may further be film coated with a protective coating which rapidly dissolves or disperses in gastric juices.

It should be noted that the above additives are not required for the stimulant composition of the present technology to have sustained release and abuse resistance properties. The stimulant prodrug of the present technology itself can control the release of the stimulant into the digestive tract over an extended period of time resulting in an improved profile when compared to immediate release combinations and prevention of abuse without the addition of the above additives. In one or more embodiments of the present technology, no further sustained release additives are required to achieve a blunted or reduced pharmacokinetic curve (e.g., reduced euphoric effect) while achieving therapeutically effective amounts of stimulant release when taken orally.

The compounds and compositions of the presently described technology can be formulated into and administered by a variety of dosage forms, preferably, through any oral routes of delivery. Once administered, the prodrugs will release amphetamine or another stimulant under digestive conditions. Any biologically-acceptable dosage form known to persons of ordinary skill in the art, now or in the future, and combinations thereof, are contemplated for use with the present technology. Examples of preferred dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, troches, lozenges, chewable lozenges, beads, powders, granules, particles, microparticles, dispersible granules, cachets, thin strips, oral films, transdermal patches, and combinations thereof. Preferred dosage forms include, but are not limited to, capsules, thin strips, fast dissolving oral films and solution formulations.

Formulations of the present technology suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which can then be placed in the feeding tube of a patient who is unable to swallow.

If the capsule form is chosen, for example, excipients used in the capsule formulation could be broken up into four separate groups: bulk agent/binder, disintergrant, lubricant and carrier. A preferred capsule formulation comprises from about 50% to about 90% by weight of a bulk agent such as various types of microcrystalline cellulose, from about 1% to about 5% by weight of a disintegrant such as croscarmellose sodium, from about 0.5% to about 2.5% of a lubricant such as magnesium stearate or other fatty acid salts. The carrier can be either hard gelatin capsules, and preferably use the smaller sized ones such as #3 or #4 hard gelatin capsules.

Soft gel or soft gelatin capsules may be prepared, for example, by dispersing the formulation of the present technology in an appropriate vehicle (vegetable oils are commonly used) to form a high viscosity mixture. This mixture can then be encapsulated with a gelatin based film using technology and machinery known to those in the soft gel industry. The individual units so formed are then dried to constant weight.

Chewable tablets, for example, may be prepared by mixing the formulations of the present technology with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film-coated tablets, for example, may be prepared by coating tablets using techniques such as rotating pan coating methods or air suspension methods to deposit a contiguous film layer on a tablet.

Compressed tablets, for example, may be prepared by mixing the formulation of the present technology with excipients intended to add binding qualities to disintegration qualities. The mixture can be either directly compressed or granulated then compressed using methods and machinery known to those in the industry. The resultant compressed tablet dosage units are then packaged according to market need, i.e., unit dose, rolls, bulk bottles, blister packs, etc.

One preferred formulation of the polar hydrophilic prodrugs, such as non-standard amino acid conjugates of amphetamine, of the present technology is a fast dissolving oral film or thin strip. Methods and other ingredients needed to make oral films or thin strips are known in the art. Potential film forming agents include pullulan, hydroxypropylmethyl cellulose, hydroxypropyl cellulose, polyvinyl pyrrolidone, polyvinyl alcohol, sodium alginate, polyethylene glycol, xanthan gum, tragacanth gum, guar gum, acacia gum, Arabic gum, polyacrylic acid, amylase, starch, dextrin, pectin, chitin, chitosin, levan, elsinan, collagen, gelatin, zein, gluten, soy protein isolate, whey protein isolate, casein, and mixtures thereof.

Also, saliva stimulating agents, plasticizing agents, cooling agents, surfactants, emulsifying agents, thickening agents, binding agents, sweeteners, flavoring, coloring agents, preservatives, or taste masking resins may be employed in the oral films or thin strips. Preferred agents include: pullulan, triethanol amine stearate, methyl cellulose, starch, triacetin, polysorbate 80, xanthan gum, maltitol, sorbitol and glycerol.

The presently described technology also contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble vitamins, such as vitamin $B_6$ and vitamin C. In contrast, hydrophilic plasticizers are used when water-insoluble vitamins are employed which aid in dissolving the encapsulated film, making channels in the surface, which aid in nutritional composition release.

It should be understood that in addition to the ingredients particularly mentioned above, the formulations of the present technology can include other suitable agents such as flavoring agents, preservatives and antioxidants. Such antioxidants would be food acceptable and could include, for example, vitamin E, carotene, BHT or other antioxidants known to those of skill in the art.

Other compounds which may be included are, for example, medically inert ingredients, e.g., solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavoring, preserving, suspending, thickening or emulsifying agents can be included.

Liquid dispersions for oral administration may be syrups, emulsions or suspensions. The syrups may contain as a carrier, for example, saccharose or saccharose with glycerol and/or mannitol and/or sorbitol. The suspensions and the emulsions may contain a carrier, for example a natural gum, agar, sodium alginate, pectin, methylcellulose, carboxymethylcellulose or polyvinyl alcohol.

The dose range for adult or pediatric human beings will depend on a number of factors including the age, weight and condition of the patient. Suitable oral dosages of the prodrugs of one stimulant of the presently described technology can be the equivalents of those typically found in treatments using that stimulant. For example, typical dosages for amphetamine salts can range from about 1 mg to about 100 mg, although higher dosages may be approved at later dates. Using the molecular weight of the prodrug of the present technology, the release percentage (% release) of amphetamine from the prodrug and desired dosage forms of the required amphetamine, the following equation can be generated:

grams of a prodrug needed=(dosage/molecular weight of amphetamine)(% release)(molecular weight of the prodrug)

Tablets, capsules, and other forms of presentation provided in discrete units conveniently contain a daily dose, or an appropriate fraction thereof, of one or more of the prodrug compounds of the invention. For example, the units may contain from about 1 mg to about 1000 mg, alternatively from about 5 mg to about 500 mg, alternatively from about 5 mg to about 250 mg, alternatively from about 10 mg to about 100 mg of one or more of the prodrug compounds of the presently described technology.

It is also possible for the dosage form of the present technology to combine any forms of release known to persons of ordinary skill in the art. These conventional release forms include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is known in the art.

Compositions of the present technology may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times.

Likewise, the compositions of the present technology may be provided in a blister pack or other such pharmaceutical package. Further, the compositions of the present technology may further include or be accompanied by indicia allowing individuals to identify the compositions as products for a prescribed treatment. The indicia may additionally include an indication of the above specified time periods for administering the compositions. For example, the indicia may be time indicia indicating a specific or general time of day for administration of the composition, or the indicia may be a day indicia indicating a day of the week for administration of the composition. The blister pack or other combination package may also include a second pharmaceutical product.

It will be appreciated that the pharmacological activity of the compositions of the present technology can be demonstrated using standard pharmacological models that are known in the art. Furthermore, it will be appreciated that the compositions of the present technology can be incorporated or encapsulated in a suitable polymer matrix or membrane for site-specific delivery, or can be functionalized with specific targeting agents capable of effecting site specific delivery. These techniques, as well as other drug delivery techniques, are well known in the art.

In one or more embodiments of the present technology, the solubility and dissolution rate of the composition can be substantially changed under different physiological conditions encountered, for example, in the intestine, at mucosal surfaces, or in the bloodstream. In one or more embodiments of the present technology, the solubility and dissolution rate of the composition can substantially decrease the bioavailability of the amphetamine, particularly at doses above those intended for therapy. In one embodiment of the present technology, the decrease in bioavailability occurs upon intranasal administration. In another embodiment, the decrease in bioavailability occurs upon intravenous administration.

For each of the described embodiments of the present technology, one or more of the following characteristics can be realized: The cardiovascular toxicity of the amphetamine prodrug is substantially lower than that of the unconjugated amphetamine and amphetamine conjugated with a standard amino acid. The covalently bound polar hydrophilic moiety, such as a non-standard amino acid moiety, reduces or eliminates the possibility of behavioral deterioration or the rebound effect. The covalently bound polar hydrophilic moiety reduces or eliminates the possibility of abuse by intranasal administration. The covalently bound polar hydrophilic moiety reduces the possibility of abuse by injection.

The presently described technology further provides methods for altering and/or delivering amphetamines and other stimulants in a manner that can decrease their potential for abuse. Methods of the present technology provide various ways to regulate pharmaceutical dosage through conjugating stimulants such as amphetamine with polar hydrophilic ligands, such as non-standard amino acids, of the present technology.

One embodiment provides a method for preventing behavioral deterioration or the rebound effect by administering to a patient in need an amphetamine prodrug composition of the present technology, which comprises at least one polar hydrophilic conjugate of amphetamine.

Another embodiment provides a method for preventing behavioral deterioration or the rebound effect by administering to a patient in need an amphetamine prodrug composition of the present technology, which comprises at least one non-standard amino acid conjugate of amphetamine.

Another embodiment provides a method for safely delivering amphetamine or another stimulant comprising providing a therapeutically effective amount of at least one polar, hydrophilic prodrug of stimulant of the present technology wherein the polar hydrophilic moiety can reduce the rate of absorption of amphetamine or another stimulant as compared to delivering the unconjugated stimulant or the stimulant conjugated with a standard amino acid, for example.

Another embodiment provides a method for safely delivering amphetamine comprising providing a therapeutically effective amount of at least one non-standard amino acid conjugate of amphetamine wherein the non-standard amino acid moiety can reduce the rate of absorption of amphetamine as compared to delivering the unconjugated amphetamine or amphetamine conjugated with a standard amino acid.

Another embodiment provides a method for reducing stimulant toxicity comprising providing a patient with at least one polar, hydrophilic prodrug of the stimulant of the present technology, wherein the polar hydrophilic moiety can increase the rate of clearance of pharmacologically active stimulant (i.e., released stimulant such as amphetamine) when given at doses exceeding those within the therapeutic range of the stimulant.

Another embodiment provides a method for reducing stimulant toxicity comprising providing a patient with at least one polar, hydrophilic stimulant prodrug of the present technology, wherein the polar hydrophilic moiety can provide a plasma release curve which does not increase above the stimulant's toxicity level when given at doses exceeding those within the therapeutic range for the unconjugated stimulant.

Another embodiment provides a method for reducing amphetamine cardiovascular toxicity comprising providing a patient with at least one non-standard amino acid conjugate of amphetamine, wherein the amino acid moiety can decrease the rate of release of amphetamine within the first a few hours of administration.

Another embodiment provides a method for reducing amphetamine cardiovascular toxicity comprising providing a patient with at least one non-standard amino acid conjugate of amphetamine, wherein the amino acid moiety can provide a plasma release curve which does not increase above the amphetamine's cardiovascular toxicity level.

Another embodiment provides a method for reducing bioavailability of stimulant a comprising providing at least one polar, hydrophilic stimulant prodrug of the present technology, wherein the stimulant prodrug can maintain a steady-state plasma release curve which provides a therapeutically effective bioavailability but prevents spiking or increased plasma concentrations compared to unconjugated stimulant when given at doses exceeding those within the therapeutic range for the unconjugated stimulant or the stimulant conjugated with a standard diamino acid, for example.

Another embodiment provides a method for reducing bioavailability of amphetamine or for preventing a toxic release profile of amphetamine in a patient, comprising providing at least one non-standard amino acid conjugate of amphetamine, wherein the conjugated amphetamine can maintain a steady-state plasma release curve which provides a therapeutically effective bioavailability but prevents spiking or increased plasma concentrations compared to amphetamine conjugated with a standard amino acid.

Another embodiment provides a method for preventing a $C_{max}$ or equivalent $C_{max}$ spike for amphetamine or another stimulant while still providing a therapeutically effective bioavailability curve comprising the step of administering to a patient at least one polar, hydrophilic prodrug of amphetamine or another stimulant of the present technology.

Another embodiment provides a method for preventing a $C_{max}$ or equivalent $C_{max}$ spike for amphetamine while still providing a therapeutically effective bioavailability curve comprising the step of administering to a patient at least one non-standard amino acid conjugate of amphetamine.

Another embodiment provides a method for preventing a toxic release profile in a patient comprising administering to a patient at least one polar, hydrophilic stimulant prodrug of the present technology, wherein the stimulant prodrug can maintain a steady-state plasma release curve which provides a therapeutically effective bioavailability but prevents spiking or increased plasma concentrations compared to unconjugated stimulant or the stimulant conjugated to a standard amino acid, particularly when taken at doses above prescribed amounts.

Another embodiment of the present technology is a method for reducing or preventing abuse of a stimulant comprising providing, administering, or prescribing a composition to a patient in need thereof, wherein said composition comprises at least one polar, hydrophilic stimulant prodrug of the present technology such that the pharmacological activity of the stimulant is decreased when the composition is used in a manner inconsistent with the manufacturer's instructions.

Another embodiment of the present technology is a method for reducing or preventing abuse of a stimulant such as amphetamine comprising consuming at least one polar, hydrophilic prodrug of the stimulant of the present technology, wherein said prodrug comprises the stimulant covalently attached to a polar hydrophilic ligand such that the pharmacological activity of the stimulant is substantially decreased when the composition is used in a manner inconsistent with the manufacturer's instructions.

Another embodiment of the present technology is a method for reducing or preventing abuse of amphetamine comprising providing, administering, consuming, or prescribing a composition to a patient in need thereof, wherein said composition comprises at least one non-standard amino acid conjugate of amphetamine such that the pharmacological activity of amphetamine is decreased when the composition is used in a manner inconsistent with the manufacturer's instructions.

Another embodiment of the present technology is a method of preventing behavioral deterioration or the rebound effect of amphetamine or stimulant treatment comprising providing, administering, or prescribing an amphetamine composition of the presently described technology to a patient in need thereof, wherein said composition comprises at least one polar hydrophilic prodrug of amphetamine that can decrease the potential of behavioral deterioration or the rebound effect from amphetamine or stimulant treatment.

Another embodiment of the present technology is a method of preventing behavioral deterioration or the rebound effect of amphetamine or stimulant treatment comprising providing, administering, consuming, or prescribing an amphetamine composition of the presently described technology to a patient in need thereof, wherein said composition comprises at least one non-standard amino acid conjugate of amphetamine that can decrease the potential of behavioral deterioration or the rebound effect from amphetamine or stimulant treatment.

Another embodiment of the present technology is a method for reducing or preventing the euphoric effect of a stimulant comprising providing, administering, or prescribing to a human or animal in need thereof, a composition comprising at least one polar, hydrophilic stimulant prodrug of the present technology that can decrease the pharmacological activity of the stimulant when the composition is used in a manner inconsistent with the manufacturer's instructions.

Another embodiment of the present technology is a method for reducing or preventing the euphoric effect of amphetamine comprising providing, administering, or prescribing to a human in need thereof, or consuming a composition comprising at least one non-standard amino acid conjugate of amphetamine that can decrease the pharmacological activity of amphetamine when the composition is used in a manner inconsistent with the manufacturer's instructions.

Another embodiment of the present technology is a method for reducing or preventing the euphoric effect of a stimulant, comprising consuming a composition comprising at least one polar, hydrophilic stimulant prodrug of the present technology that can decrease the pharmacological activity of the stimulant when the composition is used in a manner inconsistent with the manufacturer's instructions.

Another embodiment of the present technology is any of the preceding methods wherein the stimulant composition used is adapted for oral administration, and wherein the stimulant prodrug is resistant to release the stimulant from the polar hydrophilic moiety when the composition is administered parenterally, such as intranasally or intravenously. Preferably, the stimulant may be released from the polar hydrophilic moiety in the presence of acid and/or enzymes present in the stomach, intestinal tract, or blood serum. Optionally, the stimulant composition used may be in the form of a tablet, capsule, oral solution, oral suspension, thin strip or other oral dosage form discussed herein.

Another embodiment of the present technology is any of the preceding methods wherein the amphetamine composition used is adapted for oral administration, and wherein the amphetamine prodrug is resistant to release amphetamine from the non-standard amino acid moiety when the composition is administered parenterally, such as intranasally or intravenously. Preferably, amphetamine may be released from the non-standard amino acid moiety in the presence of the intestinal tract. Optionally, the amphetamine composition used may be in the form of a tablet, capsule, oral film, oral solution, oral suspension, or other oral dosage form discussed herein.

For one or more of the recited methods, the composition of the present technology used may yield a therapeutic effect without substantial euphoria. Preferably, the stimulant, such as amphetamine, composition of the present technology can provide a therapeutically equivalent AUC when compared to the stimulant alone but does not provide a $C_{max}$ which results in euphoria or an equivalent $C_{max}$.

Another embodiment of the present technology is a method for reducing or preventing abuse of stimulants such as amphetamine comprising orally administering a stimulant prodrug composition of the present technology to a patient, wherein said composition comprises at least one polar, hydrophilic stimulant prodrug of the present technology that can decrease the pharmacological activity of the stimulant when the composition is used in a manner inconsistent with the manufacturer's instructions.

Another embodiment is a method for reducing or preventing the euphoric effect of a stimulant comprising orally administering a stimulant prodrug composition of the present technology to a patient in need thereof, wherein said composition comprises at least one polar, hydrophilic prodrug of the stimulant of the present technology that can decrease the pharmacological activity of the stimulant when the composition is used in a manner inconsistent with the manufacturer's instructions.

For one or more of the recited methods of the present technology, the following properties may be achieved through conjugating amphetamine to a polar hydrophilic group or to a non-standard amino acid. In one embodiment, the cardiovascular toxicity or stress of the polar hydrophilic prodrug of, or non-standard amino acid conjugate of amphetamine of the present technology may be lower than that of the amphetamine when the amphetamine is delivered in its unconjugated state, as a compound conjugated to a standard amino acid, or as a salt thereof. In another embodiment, the possibility of behavioral deterioration is reduced or eliminated. In another embodiment, the possibility of abuse by intranasal administration is reduced or eliminated. In another embodiment, the possibility of abuse by intravenous administration is reduced or eliminated.

Another embodiment of the present technology provides methods of treating various diseases or conditions requiring the stimulation of the central nervous system (CNS) comprising administering compounds or compositions of the present technology which, optionally, further comprise commonly prescribed active agents for the respective illness or disease. For instance, one embodiment of the invention comprises a method of treating attention deficit hyperactivity disorder (ADHD) comprising administering to a patient at least one polar, hydrophilic prodrug of amphetamine of the present technology. Another embodiment of the invention comprises a method of treating attention deficit hyperactivity disorder (ADHD) comprising administering to a patient at least one non-standard amino acid conjugate of amphetamine. Another embodiment provides a method of treating attention deficit disorder (ADD) comprising administering to a patient compounds or compositions of the invention.

Another embodiment of the invention provides a method of treating narcolepsy comprising administering to a patient compounds or compositions of the presently described technology.

The presently described technology and its advantages will be better understood by reference to the following examples. These examples are provided to describe specific embodiments of the present technology. By providing these specific examples, the applicants do not limit the scope and spirit of the present technology. It will be understood by those skilled in the art that the full scope of the presently described technology encompasses the subject matter defined by the claims appending this specification, and any alterations, modifications, or equivalents of those claims.

EXAMPLE 1

Comparative Study of Pharmacokinetic Parameters of Released D-Amphetamine Following Administration of a Polar Hydrophilic Prodrug of the Non-Standard Amino Acid Type (hArg-Amp) and a Standard Amino Acid Conjugate (Vyvanse™, Lys-Amp)

The pharmacokinetic parameters of d-amphetamine following oral administration in rats of a non-standard amino acid conjugate of the present technology and a standard amino acid conjugate, Vyvanse™ (Lys-Amp), commercially available from Shire, Incorporated of Wayne, Pa. are studied in this example. The non-standard amino acid conjugate used in this example is the hydrochloride salt of hArg-Amp. The results are recorded in Table 3 below:

TABLE 3

| Parameter | Non-standard amino Acid % amp[1] | Vyvanse ™ % total Amp[2] |
|---|---|---|
| $AUC_{0-8h}$ | 94% | 100% |
| $AUC_{0-4h}$ | 77% | 100% |
| $AUC_{inf}$ | 95% | 100% |
| $C_{max}$ | 76% | 100% |
| $T_{max}$ | 400% | 100% |

[1]Percent amphetamine released relative to Vyvanse ™ (at an equimolar concentration of amphetamine contained in the non-standard amino acid prodrug compared to the total amphetamine contained in Vyvanse ™)
[2]Percent amphetamine relative to 50 mg Vyvanse ™ dose The study shows that the $C_{max}$ of a prodrug of the preset technology is significantly lower than that of Vyvanse™, a standard amino acid conjugate of d-amphetamine, which can lead to lower cardiovascular effects (blood pressure, heart rate). Quick release (higher $C_{max}$) of amphetamine has already demonstrated significant increases in blood pressure and heart rate. In certain patient populations, these cardiovascular side effects can be dose limiting or can cause the termination of stimulant therapy.

The pharmacokinetic parameters of d-amphetamine following parental administration of hArg-Amp and d-amphetamine are also studied. The study shows that little release of amphetamine (intranasal: <40% of AUC and <20% of $C_{max}$, intravenous: <50% of AUC and <40% of $C_{max}$, when compared to d-amphetamine sulfate) happens when hArg-Amp is taken through parental routes (intranasal, intravenous) due to differences in enzymes encountered in the gut versus other routes. When Adderall XR® or other controlled release formulations of amphetamine are injected or snorted, the pharmacokinetic parameters of the amphetamine are significantly altered and an individual can use these changes to produce euphoria.

EXAMPLE 2

Preparation of Boc-hArg($NO_2$)-Amp

Boc-hArg($NO_2$)—OH (2.667 g, 8 mmol) was dissolved in DMF (25 mL). EDCI (2.30 g, 12 mmol), NHS (1.012 g, 8.8 mmol), d-amphetamine (1.269 g, 9.6 mmol) and DIEA (1.138 g, 8.8 mmol) were then added sequentially. The clear reaction mixture was stirred at room temperature for 16 hrs. The reaction mixture was quenched with pH 3 water (150 mL), and the product was extracted with EtOAc (3×50 mL). The combined extracts were washed with pH 3 water followed by saturated NaCl. The EtOAc layer was dried over anhydrous $MgSO_4$. The product was recrystallized from EtOAc/hexane two times to give 2.36 g of desired protected product.

The product was analyzed using $^1H$ NMR (DMSO-$d_6$) δ. The result shows 0.9-1.1 (m, 3H, Amp $CH_3$), 1.1-1.2 (m, 2H, hArg γ $CH_2$), 1.2-1.5 (m, 13H, Boc $CH_3$, hArg (3, δ $CH_2$), 2.55-2.75 (m, 2H, Amp β $CH_2$), 3.1 (m, 2H, hArg ε $CH_2$), 3.75 (m, 1H, Amp α CH), 3.95 (m, 1H, hArg α CH), 6.65 (t, 1H, hArg guanidino NH), 7.1-7.3 (m, 5H, Amp Ar—H), 7.6-8.2 (br m, 2H, hArg guanidine NH and amide NH), 8.5 (br s, 1H, hArg NH—$NO_2$). These results are consistent with the proposed structure.

EXAMPLE 3

Preparation of hArg-Amp-2 HCl
(l-homoarginine-d-amphetamine dihydrochloride)

Boc-hArg($NO_2$)-Amp (1.5 g) was dissolved in HPLC grade MeOH (120 mL) and to the clear solution was added the Pd/C catalyst (10%, Aldrich). A small stir bar was placed in the flask and the reaction mixture was stirred under a slow stream of hydrogen overnight after incorporating the 5-6 N HCl in 2-propanol solution (1.5 mL). After the overnight reaction, the solution was filtered and the solvent evaporated. The white crystalline product was dried under vacuum to give 1.61 g of the Boc-hArg-Amp intermediate product.

The product (1.6 g) was dissolved in 80 mL of HPLC grade MeOH, and 5-6N HCl in 2-propanol (3.2 mL) was added to the solution. The reaction mixture was stirred overnight, solvent removed and re-dissolved in minimum amount of MeOH. The final product was crashed out with MTBE, and dried under vacuum at 30° C. for about 20 hours to yield 1.12 g of a white powder.

The white powder was analyzed using $^1H$ NMR (DMSO-$d_6$) δ. The result shows 0.9-1.1 (m, 3H, Amp $CH_3$), 1.1-1.2 (m, 2H, hArg γ $CH_2$), 1.35 (m, 2H, hArg β $CH_2$), 1.55 (m, 2H, hArg δ $CH_2$), 2.75 (d, 2H, Amp β $CH_2$), 3.0 (m, 2H, hArg ε $CH_2$), 3.75 (m, 1H, Amp α CH), 4.05 (m, 1H, hArg α CH), 7.1-7.2 (m, 5H, Amp Ar—H), 7.2-7.8 (br m, 3H, amide NH, HCl), 8.0 (t, 1H, hArg guanidino NH), 8.2 (br s, 2H, amide or guanidino $NH_2$), 8.75 (d, 1H, amide NH); $^{13}C$ NMR (DMSO-$d_6$) δ 21.08 (Amp $CH_3$), 21.36 (hArg γ), 28.23 (hArg δ), 32.28 (hArg β), 40.18 (Amp β), 42.19 (hArg ε), 46.88 (Amp α), 52.23 (hArg α), 126.54 (p-Ar), 128.52 (m-Ar), 129.60 (o-Ar), 139.34 (Ar), 157.61 (C=O), 167.95 (guanidino C); M+1=306. These results are consistent with the proposed structure.

EXAMPLE 4

Preparation of Cit-Amp.Hcl
(l-citrulline-d-amphetamine hydrochloride)

Boc-Cit-OH (0.500 g, 1.82 mmol) was dissolved in anhydrous THF. To this solution was added NHS (0.209 g, 1.82 mmol) followed by DCC (0.376 g, 1.82 mmol). Resulting slurry was stirred at ambient temperature overnight. In a separate flask, d-amphetamine sulfate (0.306 g, 0.83 mmol) was suspended in THF (10 mL) and NMM (0.34 mL, 3.64 mmol) was added. The activated ester was filtered directly into the amphetamine suspension and the resulting suspension was stirred overnight. The reaction was quenched with 5% $NaHCO_3$ and IPAc for 45 min. Organic solvent was then removed. The aqueous layer was then extracted 3 times with IPAc and the combined organics were washed with 5% acetic acid, 5% $NaHCO_3$ and 5% NaCl. The organic layer was then dried over $Na_2SO_4$ and solvent was removed. Crude product was re-crystallized using IPAc/heptane to yield 200 mg of a white solid. HPLC: column: YMC ODS-AQ, 5 µm, 120 Å, 4.6×250 mm; mobile phase: A=0.1% $TFA/H_2O$, B=0.1% TFA/MeCN; method: 0-15 min.: 85/15→60/40, 15-25 min.: 60/40→0/100; flow rate: 1 mL/min.; UV detection: 230 nm; retention time: 8.06 min.

10 mL of 4N HCl in dioxane were added to the 200 mg (0.200 g) Boc-Cit-Amp. The mixture was stirred at room temperature for 6 hours and solvent was removed.

EXAMPLE 5

Preparation of hCit-Amp.HCl
(l-homocitrulline-d-amphetamine hydrochloride)

Procedure as described for citrulline. However, 1,4-dioxane was used during amino acid activation and coupling reaction instead of THF. Crude product was purified via column chromatography (0-6.5% MeOH/DCM) to give 201 mg (0.49 mmol) of Boc-l-hCit-d-amphetamine (based on 500 mg of Boc-l-hCit-OH).

The Boc-protected Boc-l-hCit-d-Amp (110 mg, 0.27 mmol) was cooled in an ice-bath and 10 mL of chilled 4 N HCl/dioxane were added. The mixture was stirred for 4 h and solvent was evaporated to dryness yielding 92 mg (0.27 mmol) of l-hCit-d-Amp.HCl. HPLC: column: YMC ODS-AQ, 5 µm, 120 Å, 4.6×250 mm; mobile phase: A=0.1% $TFA/H_2O$, B=0.1% TFA/MeCN; method: 0-15 min.: 85/15→60/40, 15-25 min.: 60/40→0/100; flow rate: 1 mL/min.; UV detection: 230 nm; retention time: 8.92 min.

EXAMPLE 6

Preparation of hyPro-Amp.HCl
(2-hydroxyproline-d-amphetamine hydrochloride)

Z-l-hyPro(t-Bu)-OH (1.000 g, 3.11 mmol) was dissolved in 15 mL of anhydrous THF. NHS (0.358 g, 3.11 mmol) was added and the solution was stirred for 5 min. DCC (0.642 g, 3.11 mmol) was then added and the mixture stirred overnight at ambient temperature. In a separate flask, d-amphetamine sulfate (0.521 g, 1.41 mmol) was suspended in 15 mL of anhydrous THF and NMM (0.68 mL, 6.22 mmol) was added. The mixture was stirred for 10 min. Subsequently, the prior prepared succinimidyl ester was charged to the suspension through a sintered funnel and the mixture was stirred overnight. The reaction was quenched with 5% $NaHCO_3$ solution (75 mL). IPAc (25 mL) was added and the solution stirred for 45 min. The mixture was concentrated by evaporating most of the organic solvents. The aqueous layer was extracted with IPAc (3×100 mL). The combined organics were washed with 5% HOAc (1×100 mL), 5 $NaHCO_3$ (1×100 mL) and 5% NaCl solution (2×100 mL), dried over $Na_2SO_4$ and evaporated to dryness. Crude product was dissolved in 10 mL of $Ac_2O$ at 60° C. and 10 mL water were added while hot. The mixture was kept overnight at ambient temperature. White crystals formed which were filtered off, rinsed with water and dried in high vacuum to yield 877 mg (2.00 mmol) of Z-l-hyPro(tBu)-d-Amp.

Fully protected Z-l-hyPro(t-Bu)-d-Amp (500 mg, 1.14 mmol) was dissolved in 10 mL of MeOH. Pd/C (10 w.t.-% Pd, 250 mg) was added and the mixture stirred overnight in hydrogen atmosphere at ambient temperature. The suspension was filtered through Celite® and solvent was evaporated to dryness. Crude product was purified via column chromatography (0-2.5% MeOH/DCM) to give 96 mg (0.32 mmol) of l-hyPro(t-Bu)-d-Amp.

Hydroxyl-protected l-hyPro(t-Bu)-d-Amp (96 mg, 0.32 mmol) was cooled in an ice-bath and 5 mL of chilled TFA were added. The ice-bath was removed and the mixture was stirred overnight. The solvent was evaporated and the remaining residue was dissolved in 4 N HCl/dioxane. This process was repeated three times. The product was dried in high vacuum to yield 90 mg (0.32 mmol) of l-hyPro-d-Amp.HCl. HPLC: column: YMC ODS-AQ, 5 µm, 120 Å, 4.6×250 mm; mobile phase: A=0.1 $TFA/H_2O$, B=0.1% TFA/MeCN; method: 0-15 min.: 85/15→60/40, 15-25 min.: 60/40→0/100; flow rate: 1 mL/min.; UV detection: 230 nm; retention time: 9.61 min.

EXAMPLE 7

Preparation of Lys-ol-Co-Amp
(l-Lysinol-Co-D-Amphetamine)

Boc-l-Lys(Z)-ol (500 mg, 1.36 mmol) was dissolved in 10 mL of anhydrous dioxane. CDI was added and the mixture stirred overnight at ambient temperature. Solvent was evaporated to dryness and the remaining oily residue was dissolved in 15 mL of anhydrous THF. Amphetamine sulfate (277 mg, 0.75 mmol) and $Et_3N$ (0.40 mL, 2.86 mmol) were added and the mixture was stirred overnight at 50° C. The reaction was quenched with water and the aqueous layer extracted with IPAc (3×75 mL). The combined organics were washed with 5% HOAc, sat. $NaHCO_3$, sat. NaCl and 5% NaCl solution and dried over $Na_2SO_4$. Solvents were evaporated to dryness yielding Boc-l-Lys(Z)-ol-CO-d-Amp as a white foam. HPLC: column: YMC ODS-AQ, 5 µm, 120 Å, 4.6×250 mm; mobile phase: A=0.1% $TFA/H_2O$, B=0.1% TFA/MeCN; method: 0-15 min.: 85/15→60/40, 15-25 min.: 60/40→0/100; flow rate: 1 mL/min.; UV detection: 230 nm; retention time: 20.59 min.

EXAMPLE 8

Preparation of Carn-Amp
(O-acetyl-l-carnitine-d-amphetamine)

O-Acetyl-l-carnitine.Cl (1.000 g, 4.17 mmol) was dissolved in 12.5 mL of a mixture of DMF/dioxane/water (2:2:1). NHS (0.528 g, 4.59 mmol) and DCC (0.947 g, 4.59 mmol) were added and the mixture was stirred overnight at ambient temperature. Solvents were evaporated and the remaining residue was dried overnight in high vacuum. The crude succinimidyl ester intermediate was dissolved in 20 mL of anhydrous DMF. Amphetamine sulfate (0.700 g, 1.90 mmol) and NMM (0.92 mL, 8.34 mmol) were added and the mixture stirred overnight. Solvent was evaporated to dryness and the remaining residue was leached with IPA. Solvent was evaporated to yield Carn-d-Amp.

EXAMPLE 9

Pharmacokinetic Study of hArg-Amp Vs. Lys-Amp

Male Sprague-Dawley rats were fasted overnight and dosed by oral gavage with either l-homoarginine-d-amphetamine (hArg-Amp) or l-lysine-d-amphetamine (Vyvanse™, Lys-Amp). Water was provided ad libitum. Doses were calculated at an equivalent 1.5 mg/kg freebase equivalent of d-amphetamine. Plasma concentrations of d-amphetamine were measured using ELISA (Neogen Corp. Lexington, Ky.).

Mean plasma concentration curves (n=5) of d-amphetamine released by l-homoarginine-d-amphetamine or l-lysine-d-amphetamine are shown in FIG. 1. Pharmacokinetic(PK) parameters of this study are listed in Table 4.

TABLE 4

Pharmacokinetic Properties of hArg-Amp and Lys-Amp

| Vehicle | % AUC | $T_{max}$ | $C_{max}$ | % $T_{max}$ | % $C_{max}$ |
|---|---|---|---|---|---|
| Lys-Amp | 100% | 3 h | 44 ng/mL | 100% | 100% |
| hArg-Amp | 99% | 4 h | 44 ng/mL | 133% | 100% |

This pharmacokinetic (PK) study clearly demonstrates a shift in the $T_{max}$ for the polar hydrophilic prodrug of the non-standard amino acid type (hArg-Amp) compared to the standard amino acid (Lys-Amp). This shift may be due to a reduction in the rate of enzymatic hydrolysis of the amide bond of the non-standard amino acid attached to amphetamine vs. the standard amino acid attached to amphetamine.

Figure 2:
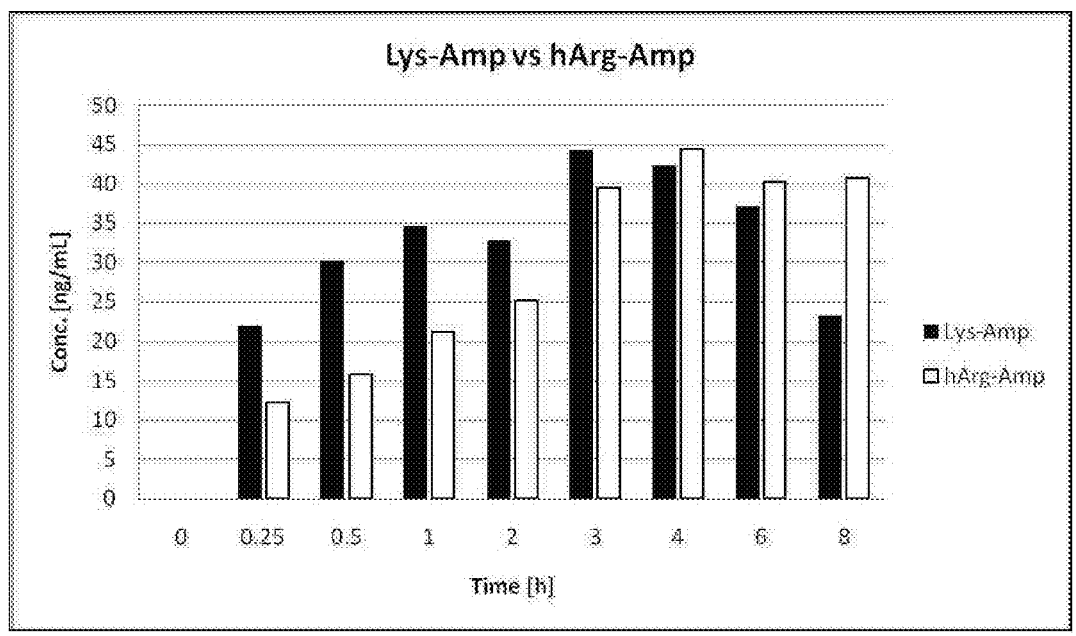
FIG. 2 compares the relative blood levels of d-amphetamine released from l-homoarginine-d-amphetamine and l-lysine-d-amphetamine.
Figure 3:
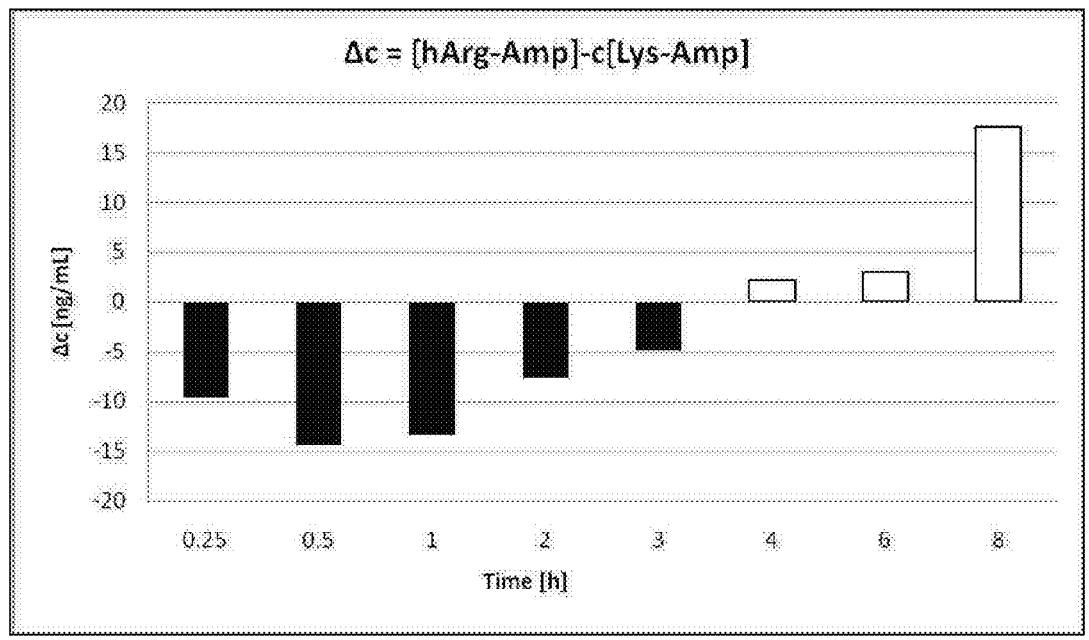
FIGS. 3 and 4 illustrate the difference in blood levels obtained from the study results shown in FIG. 2.
Figure 4:
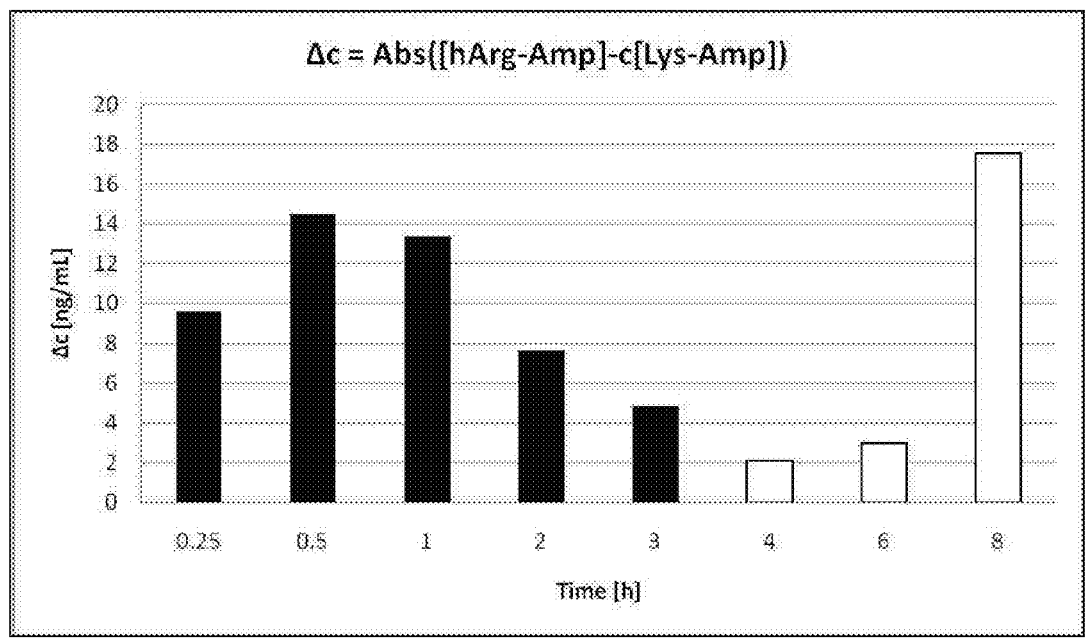

FIGS. 2-4 represent different ways to view the data reflected in FIG. 1 and Table 4. As further discussed below, these figures highlight the differences of hArg-Amp over Lys-Amp during the first several hours.

FIG. 2 demonstrates the relative blood levels of d-amphetamine released from both Lys-Amp and hArg-Amp. The graph shows that equivalent blood levels do not occur until later time points and that blood levels do not appear to spike or have a more significant $C_{max}$ than Lys-Amp. The amount of d-amphetamine released from hArg-Amp is gradual and maintains a more steady concentration over the duration of the study than did Lys-Amp. In contrast, Lys-Amp blood levels of released d-amphetamine "spiked" at 3 hours and cleared more quickly than the blood levels obtained from hArg-Amp.

FIGS. 3 and 4 show the difference in blood levels obtained from the study described in FIG. 2. As is shown, the initial blood levels for both conjugates (Lys-Amp and hArg-Amp) are very different, with hArg-Amp releasing amphetamine at a more gradual rate. These differences in blood levels become less during the more critical duration of action for stimulant treatments and more importantly, the differences are greater again at later time points suggesting that hArg-Amp maintains a more consistent dose of amphetamine when compared to Lys-Amp. The longer duration of release for hArg-Amp would suggest a much lower opportunity for behavioral deterioration to occur.

Figure 5:
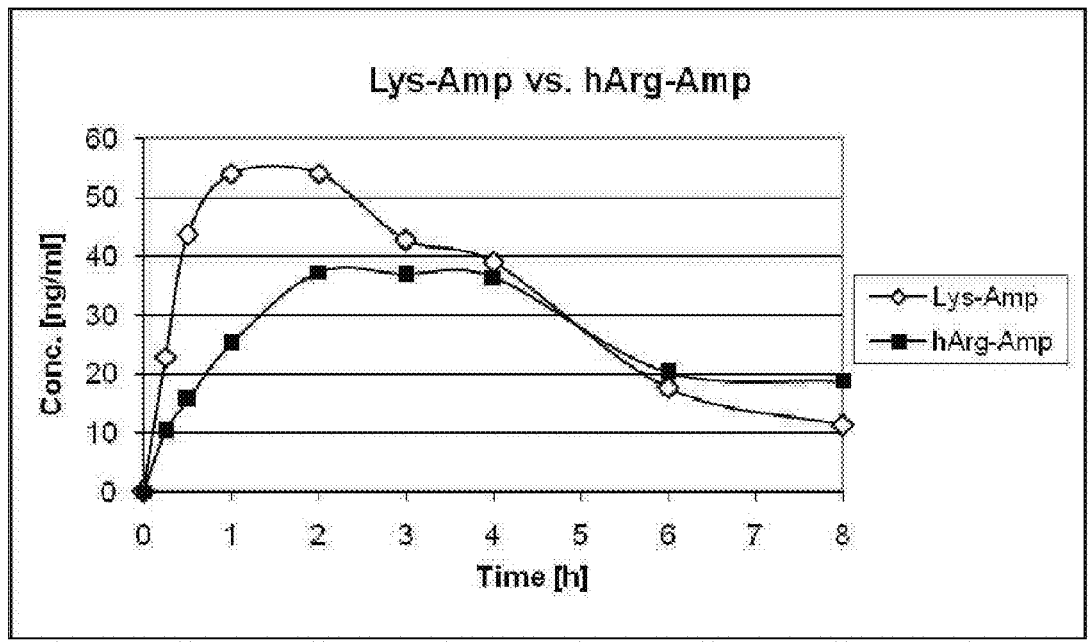
FIG. 5 compares average plasma concentrations from four (4) oral studies of rats administered l-homoarginine-d-amphetamine or l-lysine-d-amphetamine.

Other oral studies have been conducted in a similar fashion and are summarized in Table 5 below. The average PK results for four (4) oral studies (n=30 per vehicle) are recorded in FIG. 5:

TABLE 5

Average Results of 6 Oral Studies (n = 30 per compound)

| Vehicle | % AUC | $T_{max}$ | % $T_{max}$ | % $C_{max}$ | % $AUC_{0-4\,h}$ |
|---|---|---|---|---|---|
| Lys-Amp | 100% | 1 h | 100% | 100% | 100% |
| hArg-Amp | 81% | 2-4 h | 200-400% | 69% | 67% |

EXAMPLE 10

Comparative Biological Study of Lys-Amp and Cit-Amp

Figure 6:
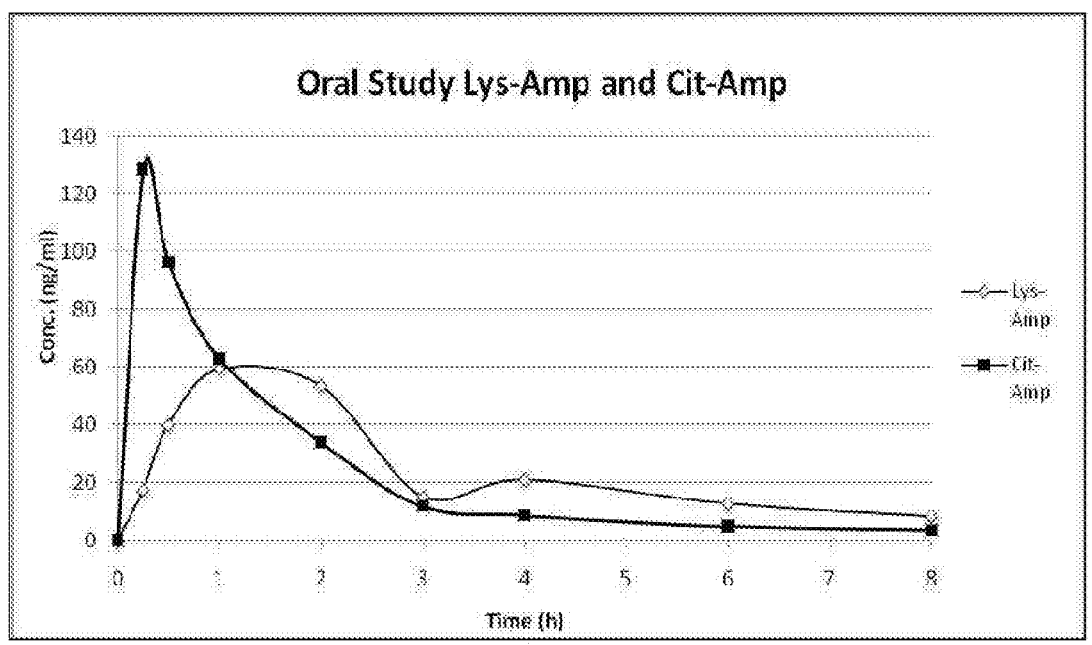
FIG. 6 compares mean plasma concentrations released from rats orally administered l-citrulline-d-amphetamine or l-lysine-d-amphetamine.

To compare the amount of release of d-amphetamine among various polar hydrophilic prodrugs, l-citrulline-d-amphetamine (Cit-Amp) was dosed with Lys-Amp in another oral pharmacokinetic study. Mean plasma concentration curves (n=5) of d-amphetamine released by Cit-Amp and Lys-Amp are shown in FIG. 6. Pharmacokinetic parameters of this study are listed in Table 6.

Direct comparison of polar hydrophilic prodrugs especially non-standard amino acid conjugates of amphetamine (Cit and hArg) demonstrate the significant ability to shift or change the pharmacokinetic properties versus the standard amino acids. All non-standard amino acids studied released amphetamine in an amount greater than 50%. Homoarginine showed $C_{max}$ levels far below that of lysine and homoarginine and citrulline significantly shifted the $T_{max}$ compared to Lys-Amp. These changes to the pharmacokinetic properties of amphetamine when conjugated to non-standard amino acids represent clinically significant changes not described or demonstrated by Lys-Amp nor described or demonstrated by other standard amino acids.

TABLE 6

Oral Properties of Lys-Amp and Cit-Amp

| Vehicle | % AUC | $T_{max}$ | $C_{max}$ | % $T_{max}$ | % $C_{max}$ |
|---|---|---|---|---|---|
| Lys-Amp | 100% | 1 h | 59 ng/mL | 100% | 100% |
| Cit-Amp | 95% | 15 min. | 129 ng/mL | 25% | 219% |

EXAMPLE 11

Pharmacokinetic Study of Lys-Amp, hCit-Amp and hArg(NO$_2$)-Amp

Figure 7:
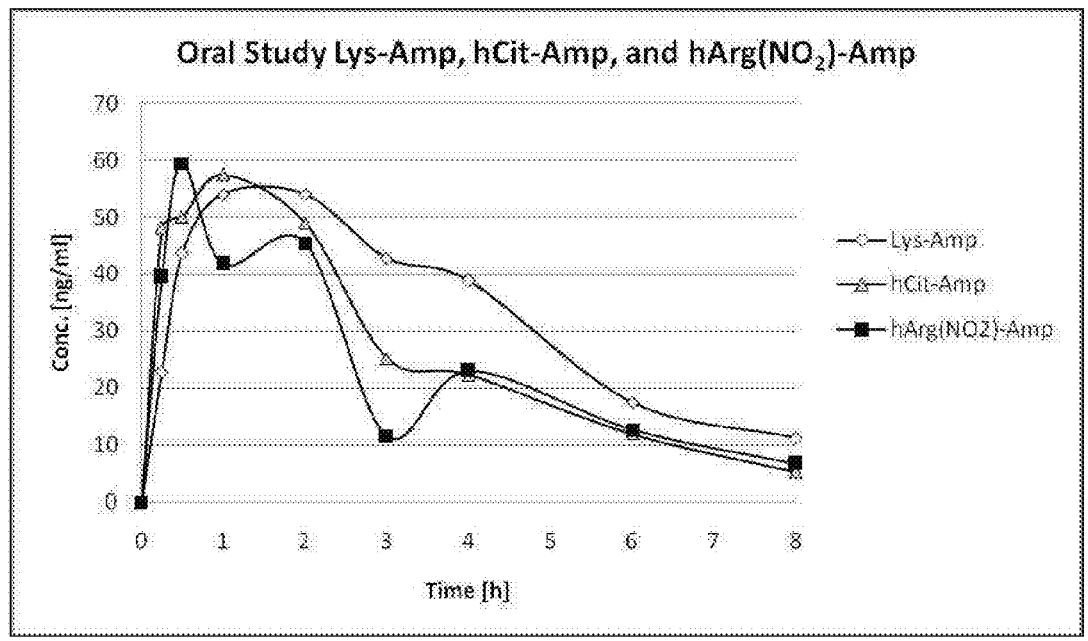
FIG. 7 compares the mean plasma concentrations of d-amphetamine released from rats orally administered l-homocitrulline-d-amphetamine, l-homoarginine($NO_2$)-d-amphetamine or l-lysine-d-amphetamine.
Figure 8:
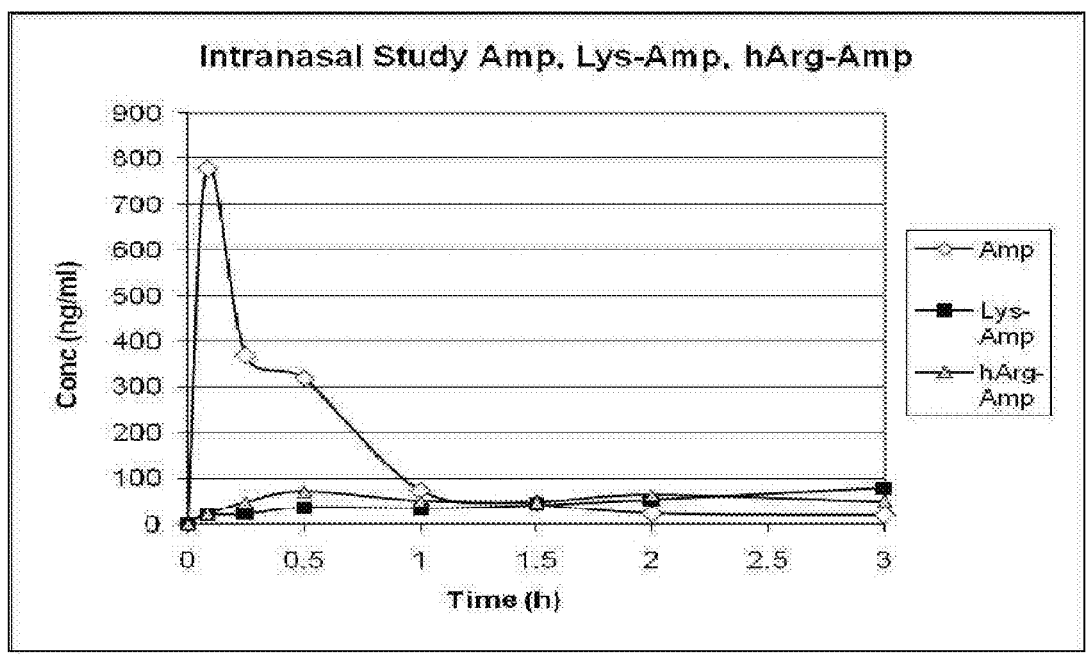
FIG. 8 compares the mean plasma concentrations of d-amphetamine released from rats intranasally administered d-amphetamine, l-homoarginine-d-amphetamine or l-lysine-d-amphetamine.

To compare the amount of release of d-amphetamine among various polar hydrophilic prodrugs, l-homocitrulline-d-amphetamine (hCit-Amp) and l-homoarginine(NO$_2$)-d-amphetamine (hArg(NO$_2$)-Amp) were dosed with Lys-Amp in another oral pharmacokinetic study. Mean plasma concentration curves (n=5) of d-amphetamine released by the amphetamine prodrugs are shown in FIGS. 7 and 8. Pharmacokinetic parameters of this study are listed in Table 7

TABLE 7

Oral Properties of Lys-Amp, hCit-Amp, Sar-Amp and hArg(NO$_2$)-Amp

| Vehicle | % AUC | $T_{max}$ | $C_{max}$ | % $T_{max}$ | % $C_{max}$ |
|---|---|---|---|---|---|
| Lys-Amp | 100% | 1 h | 54 ng/mL | 100% | 100% |
| hCit-Amp | 78% | 1 h | 57 ng/mL | NA | 105% |
| hArg(NO$_2$)-Amp | 69% | 1 h | 59 ng/mL | NA | 109% |

EXAMPLE 12

Intranasal Study of AMP, Lys-Amp and hArg-Amp

Male Sprague-Dawley rats were fasted overnight and dosed by intranasal administration with either hArg-Amp, Lys-Amp or d-amphetamine. Doses were calculated at an equivalent 1.5 mg/kg freebase equivalent of d-amphetamine. Plasma concentrations of d-amphetamine were measured using ELISA. Mean plasma concentration curves (n=5) of d-amphetamine released by hArg-Amp or Lys-Amp are shown in FIG. 8. Pharmacokinetic parameters of this study are listed in Table 8. No significant release (<50%) was observed in either hArg-Amp or Lys-Amp and less release was observed within the first hour of administration (<25%). Observed levels from Lys-Amp are significantly higher than previously published data.

TABLE 8

Intranasal Properties of d-Amp, hArg-Amp and Lys-Amp

| Vehicle | % AUC | $T_{max}$ | $C_{max}$ | % $T_{max}$ | % $C_{max}$ |
|---|---|---|---|---|---|
| d-Amp | 100% | 5 min. | 779 ng/mL | 100% | 100% |
| hArg-Amp | 42% | 0.5 h | 71 ng/mL | 600% | 9% |
| Lys-Amp | 36% | 3 h | 79 ng/mL | 3600% | 10% |

EXAMPLE 13

Intravenous Study of d-Amp, hArg-Amp, Lys-Amp

Figure 9:
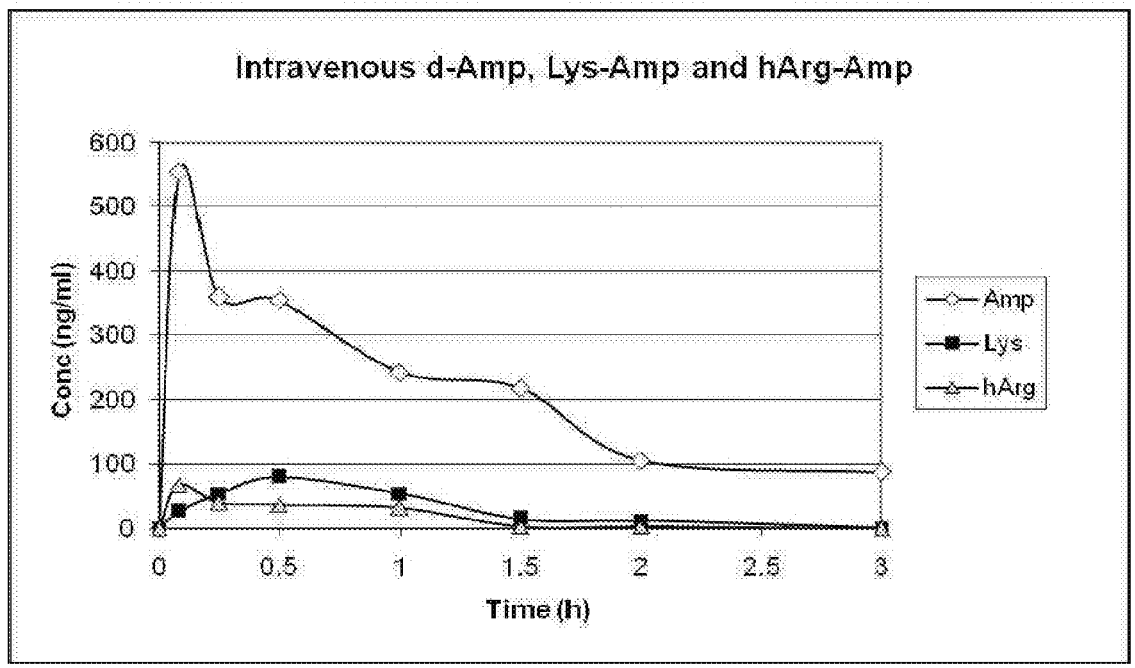
FIG. 9 compares the mean plasma concentrations of d-amphetamine released from rats intravenously administered d-amphetamine, l-homoargine-d-amphetamine or l-lysine-d-amphetamine.

Male Sprague-Dawley rats were dosed by intravenous administration through the tail vein with hArg-Amp, Lys-Amp or d-amphetamine. Doses were calculated at an equivalent 1.5 mg/kg freebase equivalent of d-amphetamine. Plasma concentrations of d-amphetamine were measured using ELISA. Mean plasma concentration curves (n=5) of d-amphetamine released by hArg-Amp or Lys-Amp are shown in FIG. 9. Pharmacokinetic parameters of this study are listed in Table 9. No significant release (<15%) was observed in either hArg-Amp or Lys-Amp though hArg-Amp was significantly less. Observed levels from Lys-Amp are significantly higher than previously published data. The initial spike in d-amphetamine released from hArg-Amp cleared quickly.

TABLE 9

Intravenous Properties of d-Amp, hArg-Amp and Lys-Amp

| Vehicle | % AUC | $T_{max}$ | $C_{max}$ | % $T_{max}$ | % $C_{max}$ |
|---|---|---|---|---|---|
| d-Amp | 100% | 5 min. | 554 ng/mL | 100% | 100% |
| hArg-Amp | 8% | 5 min. | 68 ng/mL | 100% | 12% |
| Lys-Amp | 14% | 15 min. | 79 ng/mL | 100% | 14% |

Results of the studies in above examples clearly show an unexpected change in the oral pharmacokinetic properties exhibited by polar hydrophilic prodrugs, including non-standard amino acid conjugates of amphetamine. By changing the polar hydrophilic group attached to amphetamine, the conjugates are able to shift $T_{max}$ (earlier or later), modify curve shape, lower $C_{max}$, and raise $C_{max}$. In addition, the shift in $T_{max}$ for hArg-Amp may be clinically significant in that many of the cardiovascular side effects and toxicity are related to $T_{max}$ and $C_{max}$. The results demonstrate that by using these polar hydrophilic groups, including non-standard amino acids, a shift in the $T_{max}$, with a lower $C_{max}$ occurs without changing AUC significantly. In addition, the slope of uptake of hArg-Amp vs. Lys-Amp appears to be more gradual thus leading to a slower onset which could further alleviate side effects.

The amphetamine conjugates listed above of the present technology demonstrate that by using polar hydrophilic prodrugs, a shift in the $T_{max}$ occurs while still retaining AUC and potential clinical effect. By using polar hydrophilic prodrugs, we are able to demonstrate that hArg-Amp shows little release via the IN (intranasal) and IV (intravenous) route yet still maintain a similar AUC.

In addition, the amphetamine conjugate, hArg-Amp, of the present technology demonstrates that by using non-standard amino acids, a shift in the $T_{max}$ occurs while still retaining AUC and potential clinical effect.

For example, value ranges for the pharmacokinetic parameters of amphetamine derivatives conjugated to homoarginine after oral administration when compared to the respective unconjugated amphetamine derivatives are provided in Table 10.

TABLE 10

| PK Parameter | hArg-PEA[a,b] |
|---|---|
| $AUC_{0-12h}$ | 50-200%[c] |
| $AUC_{last}$ | 50-200%[c] |
| $AUC_{inf}$ | 50-200%[c] |
| $C_{max}$ | 50-500%[c] |
| $T_{max}$ | 25-500%[c] |
| $T_{1/2}$ | 50-200%[c] |

[a]PEA = derivative of amphetamine (phenethylamine analog)
[b]PK Parameter for amphetamine derivative released from hArg-PEA conjugate expressed as percent of PK parameter for the unconjugated amphetamine derivative (both adminstered at equimolar doses)
[c]In no case shall $C_{max}$ and $T_{max}$ and $T_{1/2}$ and any AUC value for any one hArg-PEA conjugate all be within 80-125%.

The polar, hydrophilic amphetamine prodrug, such as a non-standard amino acid amphetamine conjugate, of the present technology is chemically stable to in vitro hydrolysis of the amide linkage to prevent tampering or removing the amphetamine prior to oral ingestion. Also, the controlled release of amphetamine through oral administration of the polar, hydrophilic amphetamine prodrug, such as a non-standard amino acid amphetamine conjugate, of the present technology is an inherent property of the molecule, not related to the formulation. Therefore, the prodrug of the present technology can be easily formulated to different dosage forms.

The invention is now described in such full, clear, concise and exact terms as to enable any person skilled in the art to which it pertains, to practice the same. It is to be understood that the foregoing describes preferred embodiments of the invention and that modifications may be made therein without departing from the spirit or scope of the invention as set forth in the appended claims.

What is claimed is:

1. A composition for treating a human or animal patient having attention deficit disorder or attention deficit hyperactivity disorder, comprising at least one salt of a conjugate comprising amphetamine chemically attached to homoarginine, wherein the salt is selected from an acefyllinate, 4-acetamidobenzoate, acetate, aceturate, adipate, aminosalicylate, ammonium, ascorbate, l-aspartate, besylate, bicarbonate, borate, butyrate, calcium, camphocarbonate, camphorate, d-camsylate, l-camsylate, camsylate, carbonate, cholate, cypionate, decanoate, dichloroacetate, edentate, edisylate, estolate, esylate, ethyl sulfate, fumarate, furate, fusidate, galactarate (mucate), galacturonate, gallate, gentisate, gluceptate, gluconate, glucuronate, glutamate, glutarate, glycerophosphate, glycolate, heptanoate (enanthate), hexanoate, hippurate, hybenzate, hydrobromide/bromide, hydroxide, hydroxybenzoate, iodide, isethionate, d-lactate, l-lactate, d,l-lactate, lactobionate, laurate, lithium, magnesium, maleate, malonate, mandelate, meso-tartrate, methanesulfonate, methylsulfate, myristate, napadisilate, 2-napsylate, nicotinate, octanoate, oleate, orotate, palmitate, pamoate, phenylpropionate, picrate, pivalate, potassium, propionate, pyrophosphate, salicylate, salicylsulfate, sodium, stearate, succinate, sulfosalicylate, tannate, terephthalate, thiocyanate, thiosalicylate, tosylate, tribrophenate, undecylenate, valerate, valproate, xinafoate, zinc, and mixtures thereof.

2. The composition of claim 1, wherein the homoarginine is l-homoarginine.

3. The composition of claim 1, wherein the amphetamine is d-amphetamine.

4. A composition for treating a human or animal patient having attention deficit disorder or attention deficit hyperactivity disorder, comprising a derivative of amphetamine chemically attached to homoarginine, a salt thereof, or a combination thereof, wherein the derivative of amphetamine is selected from l-amphetamine, methamphetamine, p-methoxyamphetamine, 3,4-methylenedioxyamphetamine, 2,3-methylenedioxyamphetamine, 3,4-methylenedioxymethamphetamine, 2,5-dimethoxy-4-methylamphetamine, 3,4,5-trimethoxyamphetamine, 2,4,5-trimethoxyamphetamine, 2,3,4-trimethoxyamphetamine, 2,3,5-trimethoxyamphetamine, 2,3,6-trimethoxyamphetamine, and 2,4,6-trimethoxyamphetamine.

5. The composition of claim 4, wherein the homoarginine is l-homoarginine.

6. The composition of claim 4, wherein the derivative of amphetamine is l-amphetamine.

7. The composition of claim 4, wherein the salt thereof is an acefyllinate, 4-acetamidobenzoate, acetate, aceturate, adipate, aminosalicylate, ammonium, ascorbate, l-aspartate, benzoate, besylate, bicarbonate, borate, butyrate, calcium, camphocarbonate, camphorate, d-camsylate, l-camsylate, camsylate, carbonate, cholate, citrate, cypionate, decanoate, dichloroacetate, edentate, edisylate, estolate, esylate, ethyl sulfate, fumarate, furate, fusidate, galactarate (mucate), galacturonate, gallate, gentisate, gluceptate, gluconate, glucuronate, glutamate, glutarate, glycerophosphate, glycolate, heptanoate (enanthate), hexanoate, hippurate, hybenzate, hydrobromide/bromide, hydrochloride/chloride, hydroxide, hydroxybenzoate, iodide, isethionate, d-lactate, l-lactate, d,l-lactate, lactobionate, laurate, lithium, magnesium, malate, d,l-malate, maleate, malonate, mandelate, meso-tartrate, mesylate, methanesulfonate, methylsulfate, myristate, napadisilate, 2-napsylate, nicotinate, nitrate, octanoate, oleate, orotate, oxalate, palmitate, pamoate, phenylpropionate, phosphate, picrate, pivalate, potassium, propionate, pyrophosphate, salicylate, salicylsulfate, sodium, stearate, succinate, sulfate, sulfosalicylate, tannate, d-tartrate, kartrate, d,l-tartrate, terephthalate, thiocyanate, thiosalicylate, tosylate, tribrophenate, triflate, undecylenate, valerate, valproate, xinafoate, zinc, and mixtures thereof.

8. The composition of claim 1, wherein the conjugate is l-homoarginine-d-amphetamine.

9. The composition of claim 1, wherein the composition has a reduced pharmacological activity when administered by parenteral routes.

10. The composition of claim 1, wherein the composition is in the form of a tablet, a capsule, a caplet, a troche, a lozenge, an oral powder, a solution, a oral film, a thin strip, or a suspension.

11. The composition of claim 10, wherein the tablet, troche, or lozenge is chewable.

12. The composition of claim 1, wherein the salt of the conjugate is present in the amount of from about 1 mg to about 500 mg.

13. The composition of claim 12, wherein the salt of the conjugate is present in the amount of from about 5 mg to about 250 mg.

14. The composition of claim 13, wherein the salt of the conjugate is present in the amount of from about 10 mg to about 100 mg.

15. The composition of claim 1, wherein the salt of the conjugate is in an amount sufficient to provide a therapeutically bioequivalent AUC when compared to amphetamine alone, but does not provide a $C_{max}$ spike.

16. The composition of claim 1, wherein the salt of the conjugate is in an amount sufficient to provide a therapeutically bioequivalent AUC when compared to amphetamine alone, but does not provide an equivalent $C_{max}$.

* * * * *